United States Patent
Mohammad

(10) Patent No.: US 6,302,868 B1
(45) Date of Patent: Oct. 16, 2001

(54) RETRACTABLE HYPODERMIC NEEDLE ASSEMBLY AND METHOD OF MAKING THE SAME

(76) Inventor: Owais Mohammad, 5004, Rittenhouse St., Riverdale, MD (US) 20737

( * ) Notice: Subject to any disclaimer, the term of this patent is extended or adjusted under 35 U.S.C. 154(b) by 0 days.

(21) Appl. No.: 09/316,047

(22) Filed: May 21, 1999

Related U.S. Application Data

(63) Continuation-in-part of application No. 09/218,040, filed on Dec. 22, 1998, now Pat. No. 6,162,197.

(51) Int. Cl.[7] .................................................. A61M 5/32
(52) U.S. Cl. ............................................ 604/192; 604/195
(58) Field of Search .................................. 604/192, 187, 604/194–199, 204, 212, 214, 216

(56) References Cited

U.S. PATENT DOCUMENTS

| | | | |
|---|---|---|---|
| Re. 33,585 | 5/1991 | Haber et al. | 604/198 |
| Re. 34,045 | 8/1992 | McFarland | 604/198 |
| 3,134,380 | 5/1964 | Armao | 128/215 |
| 3,892,237 * | 7/1975 | Steiner | 128/216 |
| 4,416,663 | 11/1983 | Hall | 604/163 |
| 4,425,120 | 1/1984 | Sampson | 604/198 |
| 4,564,054 | 1/1986 | Gustavsson | 141/329 |
| 4,639,249 | 1/1987 | Larson | 604/198 |
| 4,664,654 | 5/1987 | Strauss | 604/198 |
| 4,725,267 | 2/1988 | Vaillancourt | 604/198 |
| 4,735,618 | 4/1988 | Hagen | 604/192 |
| 4,737,150 | 4/1988 | Baeumle et al. | 604/198 |
| 4,758,231 | 7/1988 | Haber et al. | 604/198 |
| 4,772,272 | 9/1988 | McFarland | 604/192 |
| 4,795,432 | 1/1989 | Karczmer | 604/110 |
| 4,804,371 | 2/1989 | Vallancourt | 604/198 |
| 4,816,022 | 3/1989 | Poncy | 604/198 |
| 4,838,863 | 6/1989 | Allard et al. | 604/110 |
| 4,842,587 | 6/1989 | Poncy | 604/198 |
| 4,846,809 | 7/1989 | Sims | 604/198 |
| 4,863,436 | 9/1989 | Glick | 604/198 |
| 4,887,998 | 12/1989 | Martin et al. | 604/110 |
| 4,900,307 | 2/1990 | Kulli | 604/110 |
| 4,900,311 | 2/1990 | Stern et al. | 604/198 |
| 4,915,697 | 4/1990 | DuPont | 604/192 |
| 4,917,669 | 4/1990 | Bonaldo | 604/164 |
| 4,917,673 | 4/1990 | Coplin | 604/198 |
| 4,923,445 | 5/1990 | Ryan | 604/195 |
| 4,927,416 * | 5/1990 | Tomkiel | 604/198 |
| 4,929,237 | 5/1990 | Medway | 604/198 |

(List continued on next page.)

Primary Examiner—Anhtuan T. Nguyen
Assistant Examiner—Ann Y. Lam
(74) Attorney, Agent, or Firm—Thomas A. Powers

(57) ABSTRACT

A retractable syringe needle featuring an adjustable-length tube having a first end and a second end. The adjustable-length tube has a length which may be reversibly altered from a first contracted length to a second extended length. A syringe barrel may be secured to the first end of the adjustable length tube, and a cylindrical hub having a hollow hypodermic needle attached thereto may be secured to the second end of the adjustable-length tube. A tubular sheath is disposed around the adjustable-length tube. The tubular sheath has a first end which is rigidly connected with the first end of the adjustable-length tube and a second end having an open which is sufficiently large to allow the end of the hypodermic needle to pass therethrough. The length of the adjustable-length tube may be altered from the contracted length to the extended length. When the adjustable-length tube is contracted, the hypodermic needle is entirely disposed within the sheath. When the adjustable-length tube is extended, the end of the hypodermic needle is exposed through the opening in the second end of the sheath. A means to reversibly alter the length of the adjustable-length tube from the contracted length to the extended length at will is also provided.

47 Claims, 20 Drawing Sheets

U.S. PATENT DOCUMENTS

| | | | |
|---|---|---|---|
| 4,943,282 | 7/1990 | Page et al. | 604/198 |
| 4,966,592 | 10/1990 | Burns et al. | 604/198 |
| 4,998,924 | 3/1991 | Ranford | 604/798 |
| 5,000,740 | 3/1991 | Ducharme et al. | 604/162 |
| 5,011,475 | 4/1991 | Olson | 604/192 |
| 5,086,780 | 2/1992 | Schmitt | 604/194 |
| 5,088,986 | 2/1992 | Nusbaum | 604/198 |
| 5,092,845 | 3/1992 | Chang | 604/164 |
| 5,104,385 | 4/1992 | Huband | 604/198 |
| 5,106,379 | 4/1992 | Leap | 604/198 |
| 5,125,414 | 6/1992 | Dysarz | 128/763 |
| 5,219,338 | 6/1993 | Haworth | 664/198 |
| 5,222,947 | 6/1993 | D'Amico | 604/198 |
| 5,232,456 | 8/1993 | Gonzalez | 604/192 |
| 5,246,428 | 9/1993 | Falknor | 604/198 |
| 5,254,100 | 10/1993 | Huband | 604/198 |
| 5,279,579 | 1/1994 | D'Amico | 604/192 |
| 5,290,255 | 3/1994 | Vallelunga et al. | 604/197 |
| 5,411,487 | 5/1995 | Castagna | 604/198 |
| 5,423,758 | 6/1995 | Shaw | 604/195 |
| 5,573,513 | 11/1996 | Wozencroft | 604/198 |
| 5,591,138 | 1/1997 | Vaillancourt | 604/263 |
| 5,695,474 | 12/1997 | Daugherty | 604/162 |
| 5,695,475 | 12/1997 | Best, Jr. et al. | 604/198 |
| 5,769,826 | 6/1998 | Johnson et al. | 604/195 |
| 5,788,677 | 8/1998 | Botich et al. | 604/195 |

\* cited by examiner

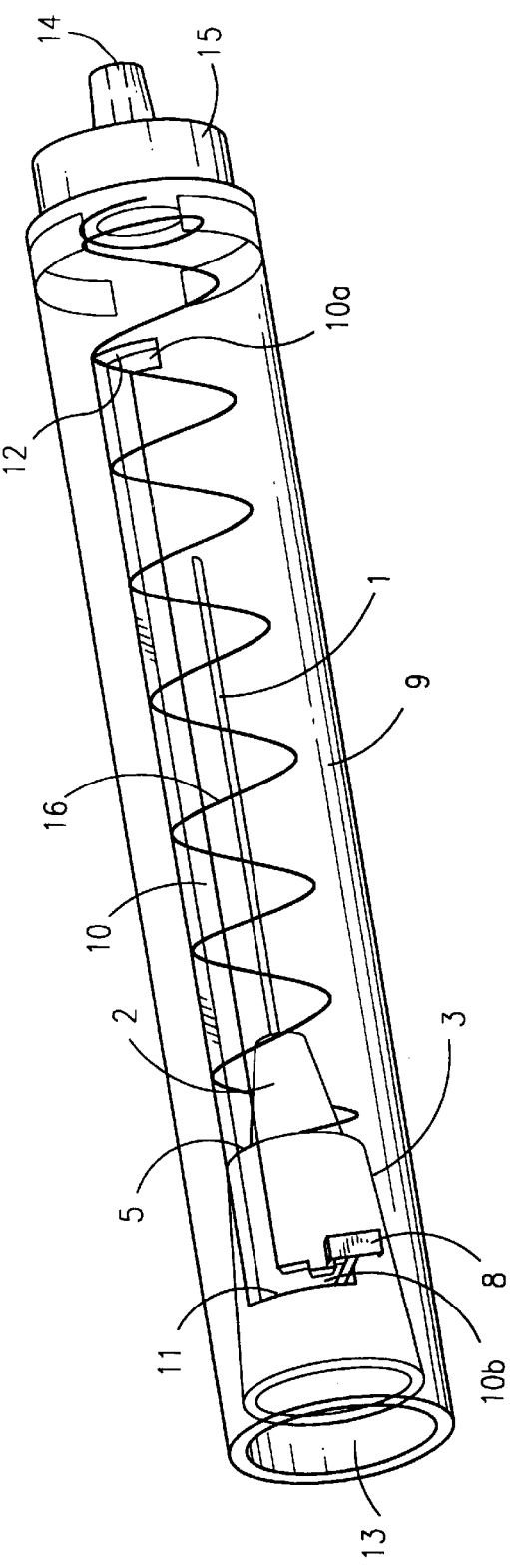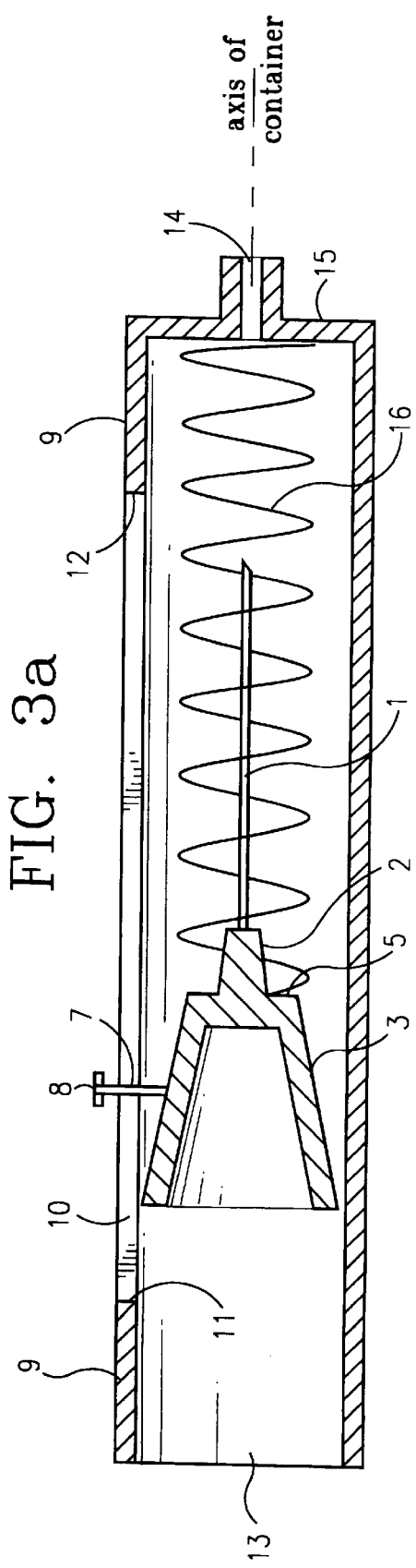

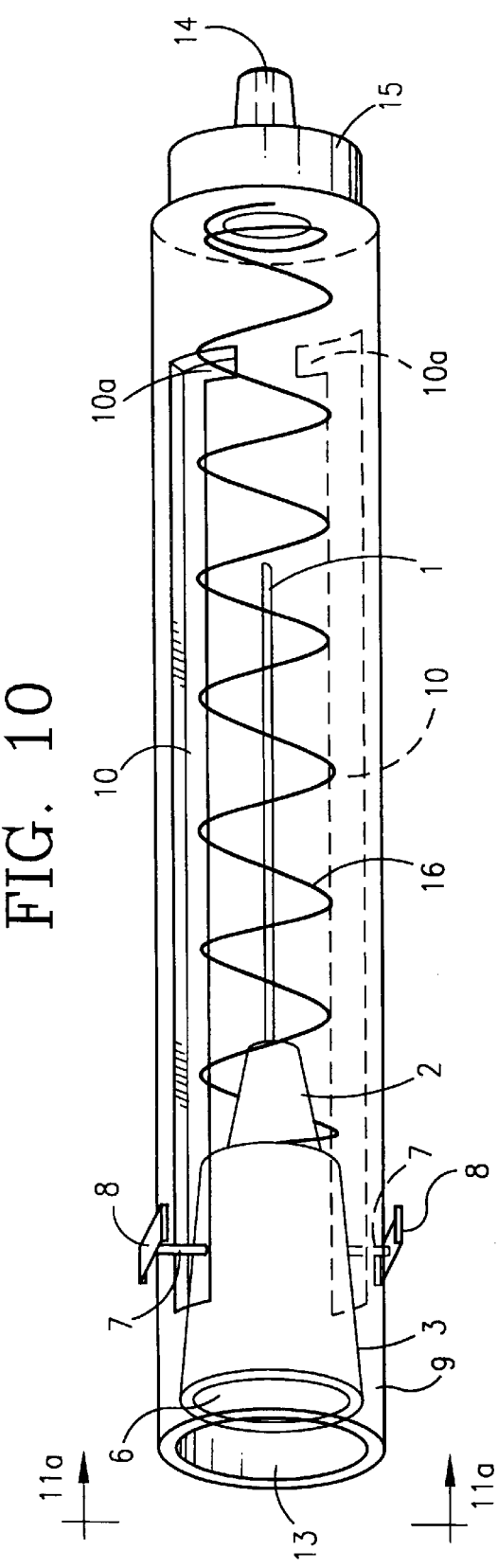
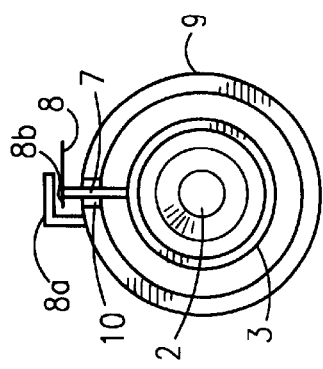
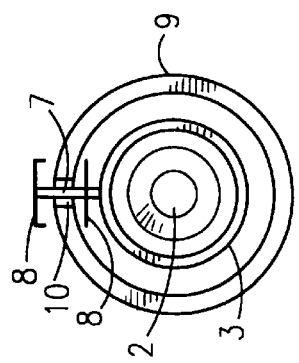
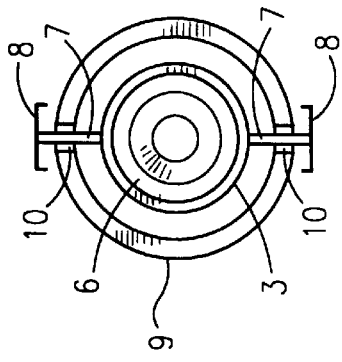

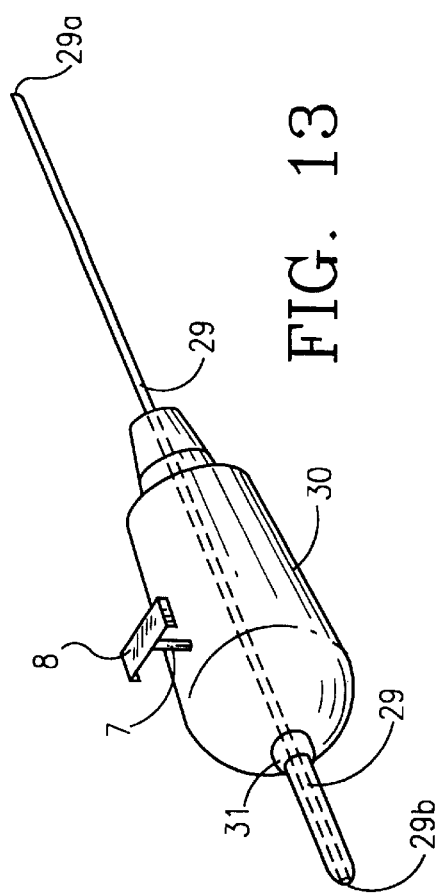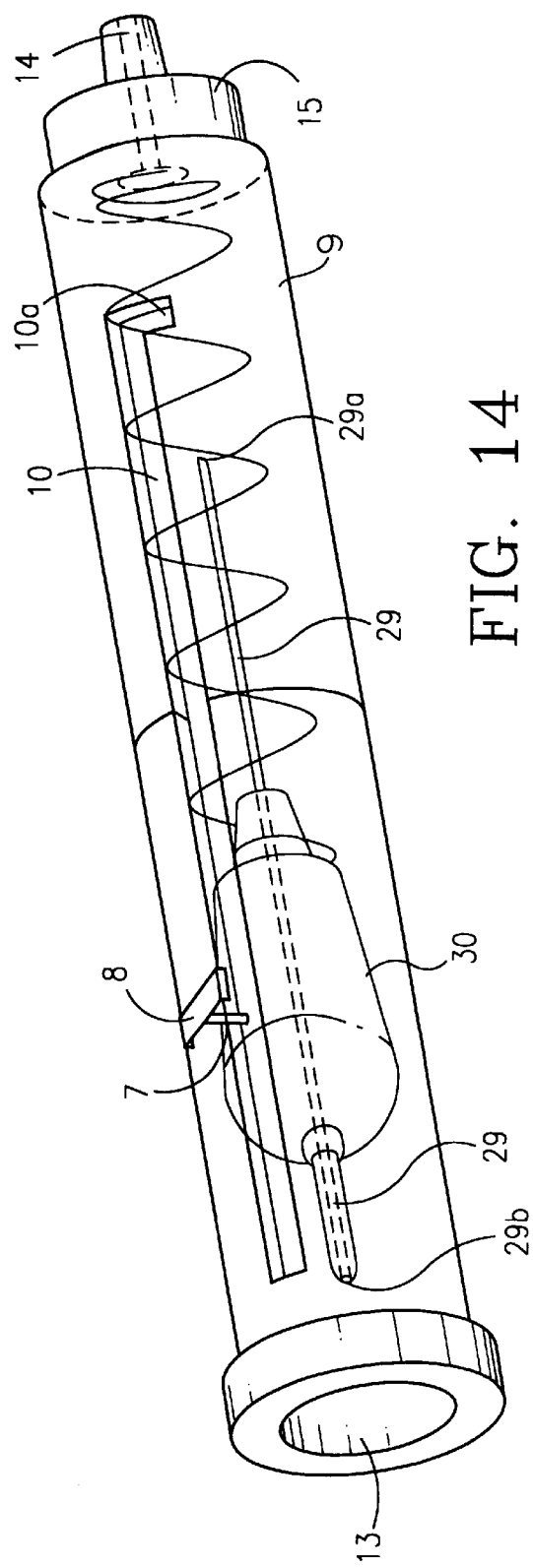
FIG. 13
FIG. 14

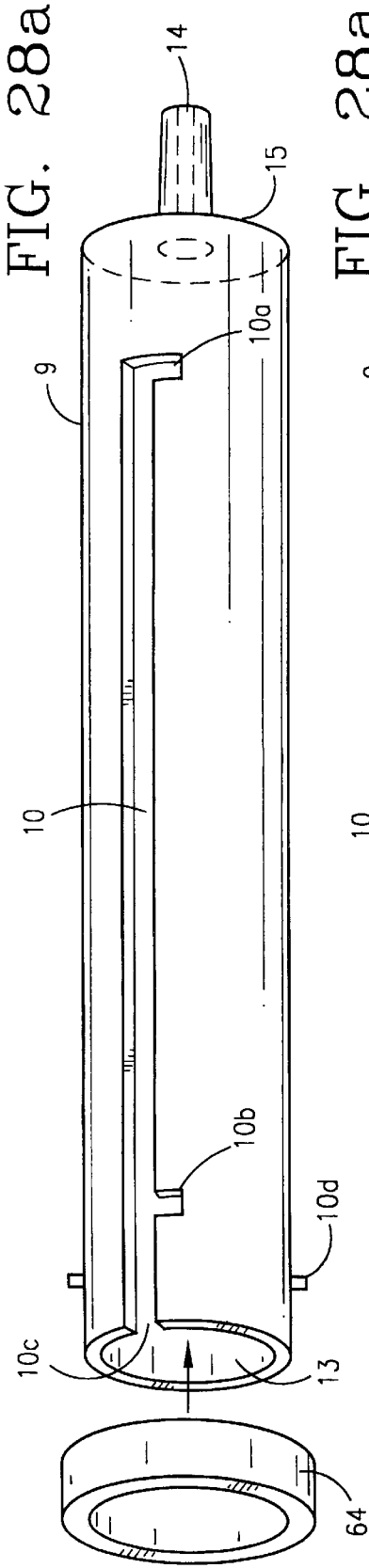
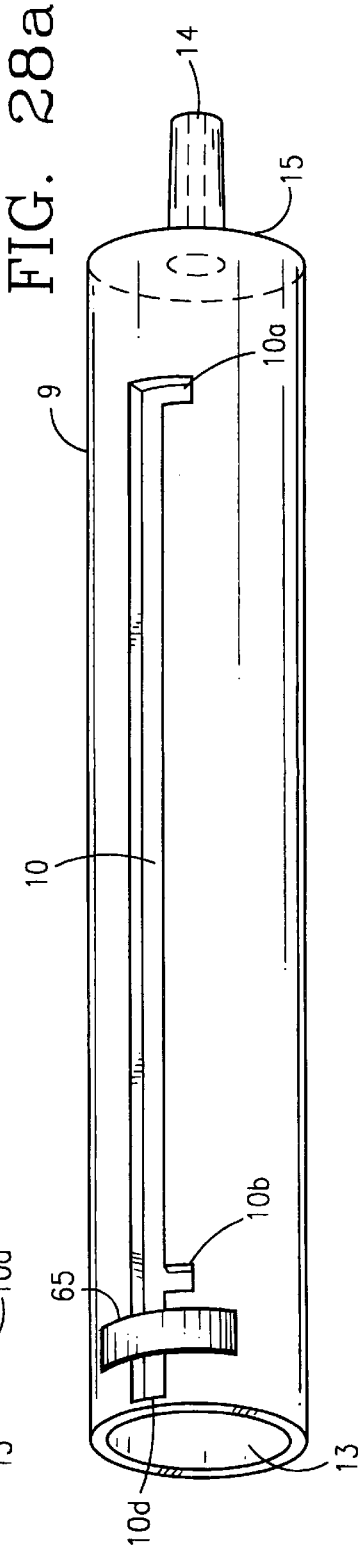
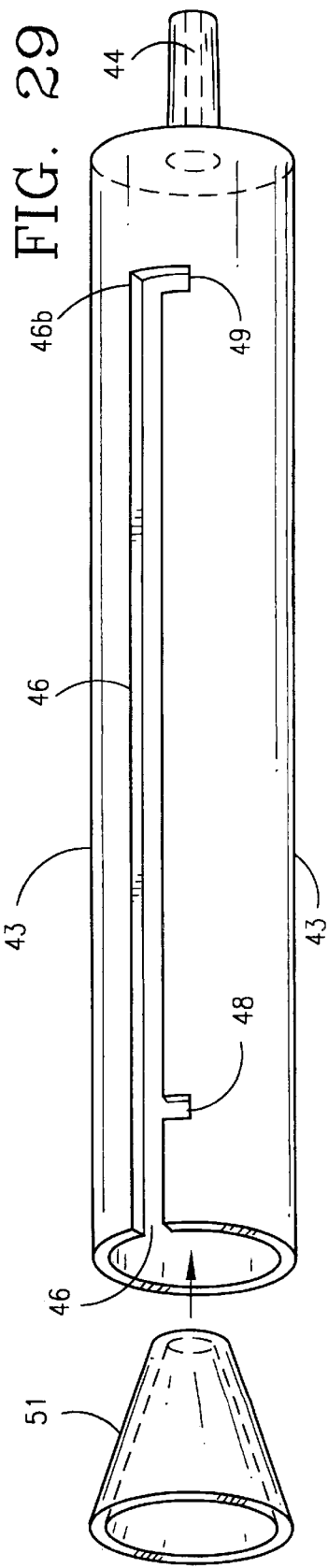
FIG. 28a   FIG. 28a   FIG. 29

RETRACTABLE HYPODERMIC NEEDLE ASSEMBLY AND METHOD OF MAKING THE SAME

This application is a continuation-in-part of U.S. patent application Ser. No. 09/218,040, filed Dec. 22, 1998, now U.S. Pat. No. 6,162,197.

BACKGROUND OF THE INVENTION

The present invention generally refers to hypodermic syringe needles for medical use. More particularly, the invention relates to hypodermic safety needles which retract into a container when not in use, preventing unintentional contact with the needle.

Prior art injection needles feature hollow needles which extend through a plastic hub. To prevent a user from accidentally pricking himself with the point of a needle, the needle is covered with a removable cover. Such covers frictionally engage the plastic hub, and may be readily removed once the needle is attached to a syringe barrel. After use, the cover may be reattached to the needle assembly, which is then separated from the syringe barrel and discarded. However, there is an unacceptable risk of accidental injury resulting from contact with the point of the needle during the recapping step. This is particularly dangerous as biological fluids contaminating the needle could enter the user's bloodstream. An improved means of covering a used injection needle is needed.

A wide variety of needles having a means for shielding a syringe needle from accidental contact with a user's fingers have been developed. For example, U.S. Pat. No. 4,900,311, issued to Stern on Feb. 13, 1990, discloses a hypodermic syringe having a syringe barrel, an injection needle attached to the syringe barrel, and a needle guard of elliptical cross section disposed around the syringe barrel. The needle guard may be moved from a first position which covers the needle to a second position which exposes the needle. When the guard is in the second position, tabs on the interior of the guard engage slots on the syringe barrel, locking the guard into position. When the tabs are released from the slots by squeezing the elliptical guard along its longitudinal axis, a spring causes the guard to move into the first position, hiding the needle. The entire syringe assembly is then discarded.

This device, while useful, does have certain drawbacks. The syringe barrel used with this assembly has a highly specialized structure; a generic syringe barrel cannot readily be substituted Also, the syringe barrel cannot readily be sterilized and reused. No provision for separation of the needle from the syringe barrel without removing the syringe needle from the protective needle guard is provided. Finally, there is the risk of accidentally squeezing the elliptical needle guard, causing the spring to move the needle guard into a position which conceals the needle prior to use of the needle.

U.S. Pat. No. 4,664,654, issued to Strauss on May 12, 1987, discloses a two piece needle shield comprising a sliding member and a stationary member. A latch holds the sliding member in position. When the latch is released, a spring causes the sliding member to retract inside the stationary member, exposing the needle. However, this device causes the user to place his hand in proximity to the needle at the time it is exposed, increasing the likelihood of injury from accidental contact with the needle.

U.S. Pat. No. 5,246,428, issued to Sep. 21, 1993, discloses a needle safety mechanism comprising a base adapted to be fixed with respect to the needle, and a sheath which is movable between a first position which exposes the needle and a second position which covers the needle. A latch cooperative between the base and the sheath may be used to releasably latch the sheath in the position which covers the needle. A spring biases the sheath into the needle covering position. No mechanism for latching the sheath in a position which exposes the needle is provided, however. This may be an inconvenience for workers who wish to see the precise spot where they are admitting an injection.

U.S. Pat. No. 5,279,579, issued to D'Amico on Jan. 18, 1994, discloses a self-capping injection needle assembly which includes a hub slidably positioned within a cylindrical cover adapted to receive a syringe barrel and a needle mounted on the hub. A spring biases the hub into a position in which the needle is contained within the tubular cover. When the spring is compressed, the hub may slide into a position which exposes the needle. The hub includes a pin which slidably engages a longitudinal groove in the tubular cover. The groove includes a transverse leg adapted to receive the pin. When the pin is positioned in the transverse leg, the hub is releasably locked into a position which exposes the needle. The hub has a threaded female joint which may be screwed onto a syringe barrel having a corresponded threaded male joint. Different size tubular covers may be used for different size syringe barrels.

This device has certain disadvantages. First, in a medical environment time is often a critical factor. A more rapid method of affixing a needle to a syringe barrel than screwing it on is desirable. Also, only syringe barrels with a specific type of joint adapted to mate with the hub are usable with this device. Most commonly used medical syringe barrels have frusto-conical tips which frictionally engage syringe needle hubs having frusto-conical cavities therein; such commonly used barrels cannot be used with the threaded connections envisioned by D'Amico. D'Amico requires that a hub having a specific diameter must be used with a tubular cover having an inner diameter which is substantially equal to the hub diameter. Most commonly available syringe needle hubs have a single standard size, and cannot be used with a range of tubular cover sizes. Therefore, D'Amico's invention necessitates creation of a range of expensive and specialized syringe needles having a range of hub sizes. Also, since the diameter of D'Amico's hub is very nearly equal to the interior diameter of the tubular cover, it is difficult to insert a hub having a protruding pin into the cover. An easy method of assembling such a device is desirable.

U.S. Pat. No. 5,219,338, issued to Haworth on Jun. 15, 1993, and U.S. Pat. No. 5,695,474, issued to Daugherty on Dec. 9, 1997, disclose syringe assemblies in which one end of a retractable sheath is secured to a syringe barrel. The sheaths have circumferential accordion-like pleats which may be folded or unfolded. When the pleats are unfolded, the sheath is in an extended configuration, and covers a hypodermic needle secured to the syringe barrel. When the pleats are folded, the sheath is contracted so as to expose the needle. However, existing syringe barrels either cannot be used with this system, or they must be modified by securing a sheath to the exterior of the barrel before use with this system. Additionally, a wide variety of sheath sizes (one for each size syringe barrel) must be maintained in stock for such a retrofitting operation to be feasible.

There is a long-felt need in the art for a safety needle assembly having a retractable needle which may be easily assembled, and which may be used with commonly available syringe barrels having frusto-conical tips which frictionally engage a syringe needle assembly. The required safety needle assembly must also avoid the other disadvantages of known prior art devices. It is an object of this invention to provide such safety needle assemblies.

SUMMARY OF THE INVENTION

The present invention provides disposable hypodermic syringe needles which retacts into a container for safe disposal. In a first embodiment, the container features a tubular wall having a longitudinal slit therethrough. One end of the container is open so that a syringe barrel may be received therein. The second end of the container has an opening which is sufficiently large to receive a hypodermic needle, but too small to receive a syringe barrel. A hypodermic needle assembly is contained within the container. This assembly features a hypodermic needle which is affixed to a hub. An annular sleeve defining a frustoconical cavity surrounds the periphery of the hub. The cavity in the annular sleeve is designed to frictionally engage a frusto-conical tip of a syringe barrel. A spring engages the hub of the needle assembly and a ridge on the interior of the wall of the second end of the container. This spring biases the hub away from the second end of the container so that the needle attached to the hub is hidden within the container. When the spring is compressed, the needle is able to pass through the opening of the second end of the container. A pin attached to the annular sleeve is slidably engaged by the longitudinal slit in the container wall, holding the needle within the container while allowing it to slide back and forth. A knob mounted on the pin is positioned outside the container. The knob is too large to pass through the longitudinal slit, and acts to position the hub of the needle along the axis of the container. When the knob is pushed toward the second end of the container, the hub moves toward the second end of the container, compressing the spring and causing the needle to emerge through the second open end of the container. A means for reversibly engaging the knob when the spring is compressed is also provided. This allows the needle to be retained in an exposed position.

The needle may be frictionally secured to a syringe barrel having a plunger slidably mounted therein More specifically, a syringe barrel having a frusto conical tip is secured to the needle assembly by inserting the frusto-conical tip of the syringe barrel into the cavity of the annular sleeve until the barrel tip is frictionally secured to the barrel sleeve. Additional features of the invention will be described in the detailed description of the preferred embodiments. Any syringe barrel having an appropriately shaped tip may be used with the inventive needle assembly.

In a second embodiment, the retractable syringe needle of the invention features a adjustable-length tube having a first end and a second end. The adjustable-length tube has a length which may be reversibly altered from a first contracted length to a second extended length. A syringe barrel having a frustoconical tip may be secured to the first end of the adjustable-length tube, and a cylindrical hub having a hollow hypodermic needle attached thereto may be secured to the second end of the adjustable-length tube. The interior of the syringe barrel is in fluid contact with the interior of the a hollow hypodermic needle through the adjustable-length tube. A tubular sheath is disposed around the adjustable-length tube. The tubular sheath has a first end which is rigidly connected with the first end of the adjustable-length tube and a second end having an opening which is sufficiently large to allow the end of the hypodermic needle to pass therethrough. The length of the adjustable-length tube may be altered from the contracted length to the extended length. When the adjustable-length tube is contracted, the hypodermic needle is entirely disposed within the sheath. When the adjustable-length tube is extended, the end of the hypodermic needle is exposed through the open in the second end of the sheath.

The length of the adjustable-length tube is altered using a knob or pin mounted on the cylindrical hub. This knob or pin slidably engages a longitudinal slot in the tubular sheath. A thumbrest attached to the knob or pin is accessible by the user from outside the sheath. The thumbrest may be used to reversibly push the knob or pin along the length of the slot from a first position near the first end of the tubular sheath to a second position near the second end of the tubular sheath. The thumbrest is too large to pass through the longitudinal slot, and acts to position the hub of the needle along the axis of the tubular sheath. When the knob or pin is near the first end of the tubular sheath, the adjustable-length tube is compared and the hypodermic needle is concealed within the sheath. When the knob is pushed toward the second end of the container, the hub moves toward the second end of the container, elongating the adjustable-length tube and causing the needle to emerge through the opening in the second end of the sheath. A means for reversibly locking the knob in either the first position near the first end of the tubular sheath or the second position near the second end of the tubular sheath is also provided.

The needle assemblies of this invention may also be attached to an IV tube and used for intravenous administration of fluids, if desired. Also a modified needle assembly having a double-ended hypodermic needle which is affixed to s hub may be used to withdraw samples of venous blood.

DESCRIPTION OF THE DRAWINGS

FIGS. 3 and 3a shows a retractable hypodermic safety needle within a container, with the needle in a configuration.

FIGS. 10 and 11a, 11b and 11c show a modified version of the apparatus of FIG. 3.

FIG. 13 shows a modified version of the needle assembly of FIG. 1, for use in taking blood samples.

FIG. 14 shows an apparatus for taking blood samples, using the needle assembly of FIG. 13.

FIG. 28*a* shows a variant of the container of FIG. 2.

FIG. 28*b* shows a second variant of the container of FIG. 2.

FIG. 29 shows a modified tubular sheath for use in the apparatus of FIG. 17.

DETAILED DESCRIPTION OF THE PREFERRED EMBODIMENTS

Figure 1:
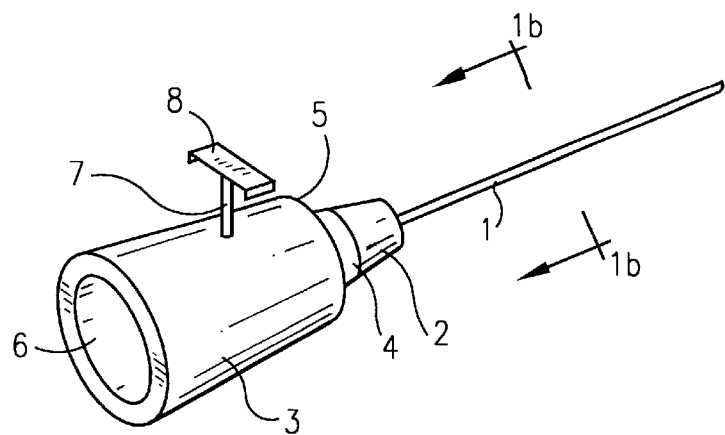
FIGS. 1, 1a, and 1b illustrate a hypodermic needle for use in the syringe assembly of this invention.
Figure 1A:
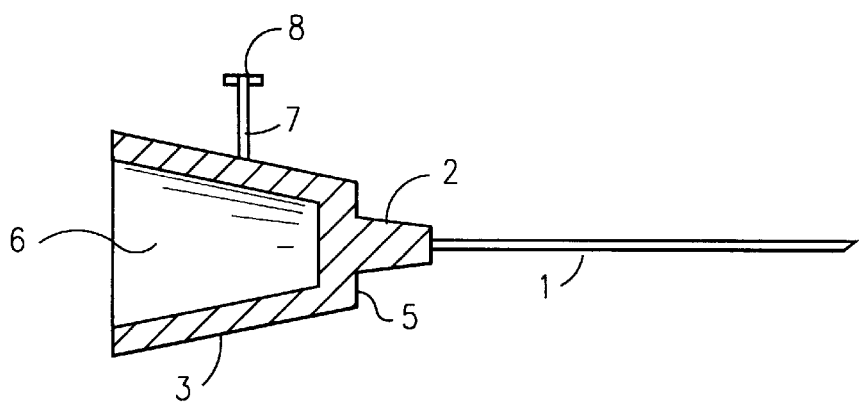
Figure 1B:
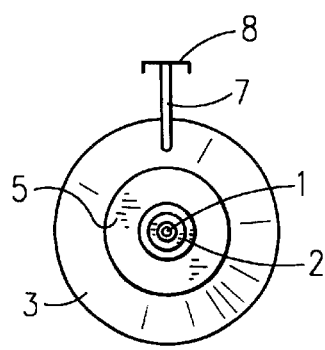

A fist embodiment of the invention will now be described FIG. 1 illustrates a hypodermic needle for use in the retractable needle assembly of this invention. Needle 1 is affixed to hub 2. A hollow bore runs longitudinally through needle 1 and hub 2. An annular sleeve 3 is affixed to the outer periphery 4 of hub 2. A ledge 5 encircling hub 2 is defined by the edge of sleeve 3. Sleeve 3 defines a frusto-conical cavity 6 adapted to frictionally engage a frustoconical tip of a syringe barrel, as shown in the cross-sectional view of FIG. 1*a*. A pin or knob 7 is affixed to the outer surface of sleeve 3. A crosspiece 8 is mounted on pin 7. Crosspiece 8 should be positioned so that, when viewed along the axis of needle 1, piece 8 and pin 7 intersect at a right angle (FIG. 1*b*). Although pin 7 and crosspiece 8 may be manufactured separately and secured together, it is preferred that 7 and 8 be manufactured as a single piece.

The manner in which needle 1 is affixed to hub 2 is not particularly limited. The needle 1 may be secured to hub 2 by providing a male joint on one end of the needle. A female joint is provided on the hub. The female joint on the hub is then secured to the male joint on the needle so as to provide a leakproof seal. One way of doing this is to provide a treaded female joint on the hub, and a threaded male joint on the needle. The threaded male and female joints may then be screwed together. Alternatively, a waterproof and biocompatible adhesive material may be used to secure the female joint to the male joint. An additional possibility is that the hub 2 may be molded around the needle 1. Similarly, sleeve 3 may be joined to hub 2 in any of several ways. Sleeve 3 and hub 2 may be molded as an integral unit. Alternatively, sleeve 3 and hub 2 may be molded separately, and then joined together. For example, a threaded female joint may be provided on the sleeve, and a threaded male joint on the hub. The threaded male and female joints may then be screwed together. Alternatively, a waterproof and biocompatible adhesive material may be used to secure the female joint to the male joint.

Figure 2:
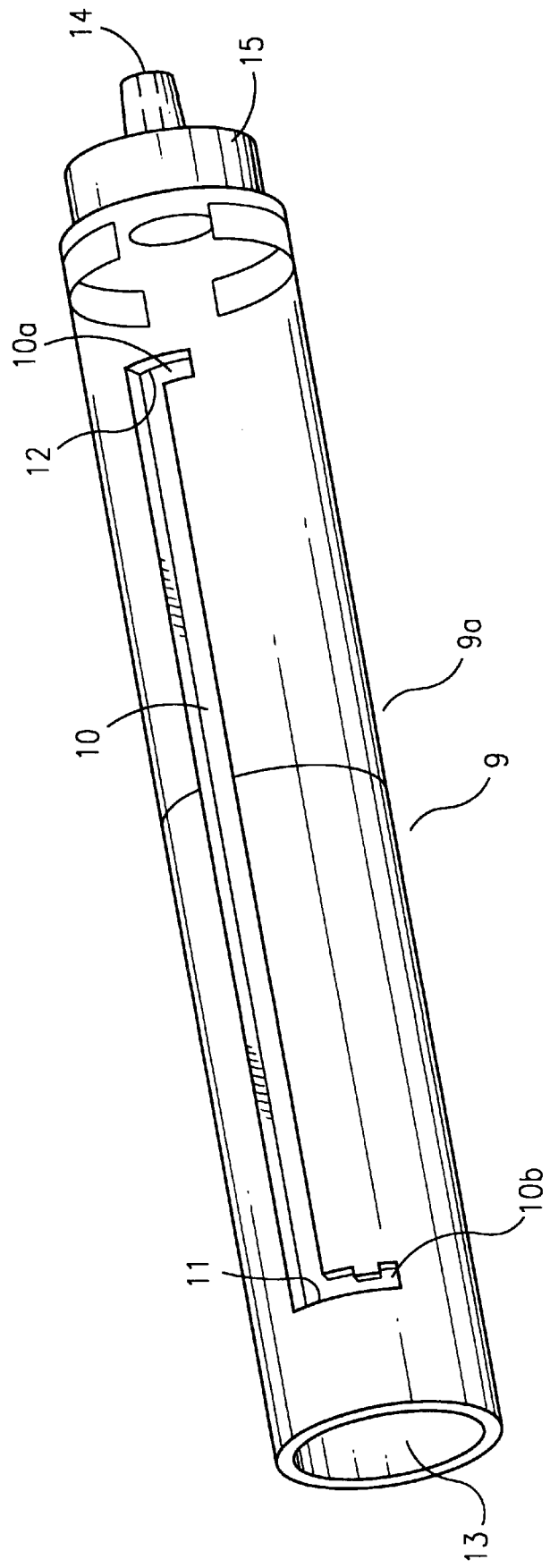
FIG. 2 shows a container designed to contained the needle of FIG. 1.

FIG. 2 shows a grooved container designed to contain the needle of FIG. 1. The container has a tubular wall 9 having a longitudinal slit 10 therethrough A first end of the container has an opening 13 adapted to receive a syringe barrel. The second end of the container has an opening 14 which is large enough to allow needle 1 to pass therethrough, but too small to admit a syringe barrel or a human finger. A ledge 15 on the second end of the container runs from the interior of wall 9 to the edge of opening 14. Slit 10 runs from a point near the first end of the container, without reaching the first end of the container, to a point near the second end of the container, without reaching the second end of the container. A second slit 10*a*, running a part of the way around the circumference of wall 9, intersects slit 10 near the second end of the container. If desired, an additional slit 10*b* may intersect slit 10 near the first end of the container.

FIG. 3 shows how the needle assembly of FIG. 1 is contained within the container of FIG. 2. The needle assembly is positioned within the container with pin 7 slidably engaging slit 10. Crosspiece 8 helps to retain pin 7 within slit 10. Piece 8 is sufficiently large that it cannot pass through slit 10 into the interior of the container, and is rigidly secured to a defined position along the length of pin 7, where the defined position on pin 7 is chosen so that hub 2 of the needle assembly is positioned along the cylindrical axis of the container, shown in the cross-sectional view of FIG. 3*a*. More particularly, the distance between the axis of hypodermic needle 1 and crosspiece 8 is equal to the one half the external diameter of the wall 9 of the container. This retains needle 1 along the axis of the container. Removal of knob 8 would allow pin 7 to slip out of slot 10, causing hub 2 to 11 against the side of wall 9. Openings 13 and 14 may be covered by a cap when the device is not in use. These caps may screw onto the ends of the container, or they may snap onto the ends of the container.

A needle having a hub of any desired size may be used in a container having any desired radius without losing the desired axial orientation of needle 1 by simply changing the distance between the axis of needle 1 and crosspiece 8. This makes it unnecessary to manufacture a wide variety of needle hubs, with each needle hub being reserved for a different container size, as required by D'Amico.

Figure 4:
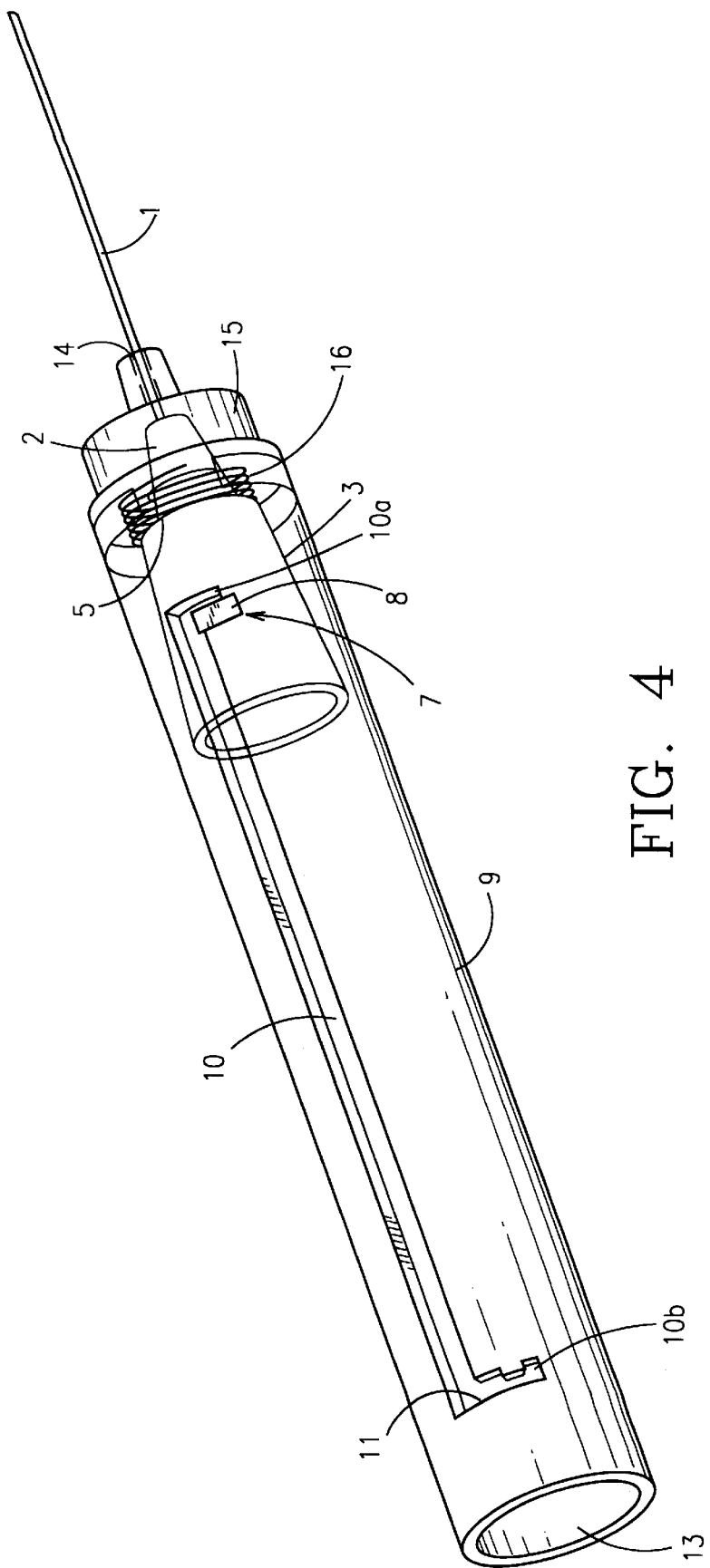
FIG. 4 shows a retractable hypodermic safety needle within container, with the needle in an exposed configuration.

A spring 16 is also positioned within the container. A first end of spring 16 engages ledge 15 at the second end of container 1, while the second end of spring 16 engages ledge 5 encircling hub 2. The spring acts to bias hub 2 away from the second end of the container so that needle 1 is effectively concealed within the container. This allows the user to effectively handle the assembly without pricking his fingers. When one is ready to use the needle, needle 1 may be exposed by pushing hub 2 toward the second end of the container. This is most easily done by manually sliding crosspiece 8, attached to pin 7, along slot 10 with the user's thumb or finger. As hub 2 approaches the second end of the container, spring 16 is compressed and needle 1 passes through opening 14 in the container and is exposed. Since needle 1 is directed along the axis of the container, it is very easy to direct the needle through opening 14. When pin 7 reaches end 12 of slot 10, pin 7 is pushed sideways into slot 10*a*. Slot 10*a* acts as a stop, preventing spring 16 from decompressing and causing needle 1 to retract into the container. An illustration of the needle assembly in this configuration is shown in FIG. 4. This has the great advantage that one may expose a sheathed needle without having to position one's fingers near the needle itself as is done when exposing the shed needle described by Strauss (vide supra). Teeth or prongs 10e on the sides of slot 10a may be used to narrow the opening of slot 10a to slightly less than the width of the pin 7, so that the knob snaps into place when it is moved into one of slot 10a. This prevents the knob from accidentally sliding into or out of the slot. If an additional slit 10a is present near the first end of the container, pin 7 may be pushed into the additional slit 10a near the first end of the contained when the spring is not compressed to prevent 10a from being compressed accidentally. Similarly, if slit 10b is present, pin 7 may be pushed into slit 10b prior to exposing the needle by compressing the spring. This is a safety measure to prevent accidental exposure of the needle.

Figure 9A:
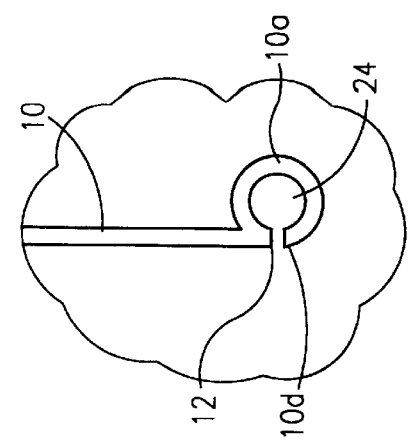
FIGS. 9a through 9c show various embodiments of locking mechanisms to hold a retractable needle in an exposed configuration.
Figure 9B:
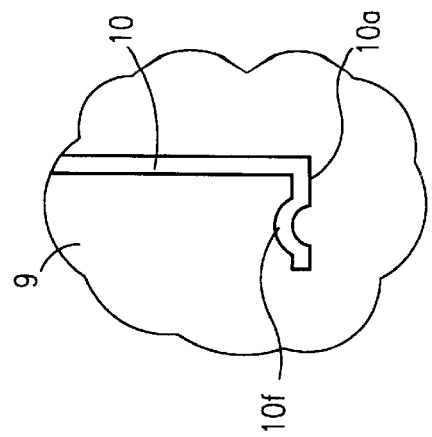
Figure 9C:
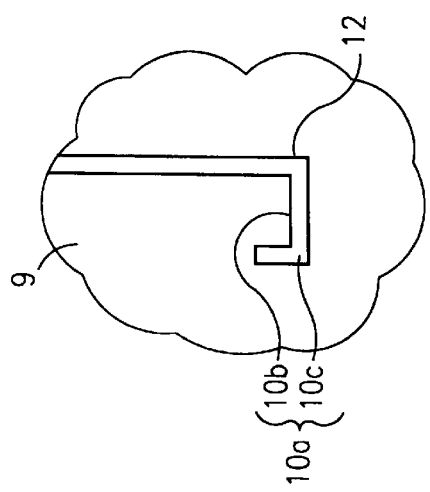

As shown in FIGS. 1 through 4, slot 10a is a simple transverse slot which intersects slot 10 at a right angle. While this is an effective arrangement, other configurations of slot 10a are possible. Three such arrangements are shown in FIGS. 9a through 9c. In FIG. 9a, slot 10a is configured as a T-shaped notch. This T-shaped notch comprises a fist transverse leg 10b which intersects slot 10, and a second leg 10c which intersects the transverse leg and is substantially parallel to slot 10. If desired, transverse leg 10b and leg 10c may be configured as an L-shaped notch, as shown in FIG. 9b. The notches of FIGS. 9a and 9b operate in the following manner. Hub 2 is moved forward within the container until pin 7 reaches end 12 of slot 10. At this point, the needle is rotated by pushing pin 7 into transverse leg 10b of slot 10a until the pin reaches the point where legs 10b and 10c intersect. At this point, spring 16 biases the hub 2 away from ridge 15, causing pin 7 to enter leg 10c of slot 10a. Leg 10c acts as a stop, preventing spring 16 from decompressing further and causing needle 1 to retract into the container. Leg 10c also prevents the user from accidentally pushing pin 7 out of slot 10a.

Figure 9D:
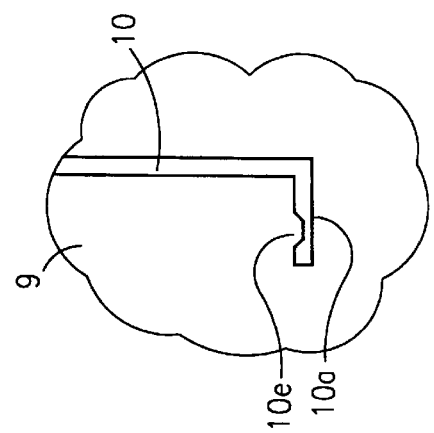
Figure 9E:
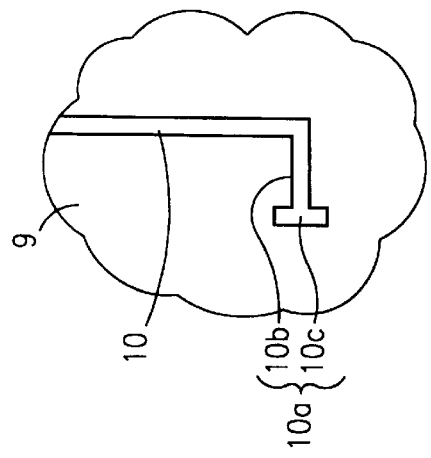
Figure 9F:
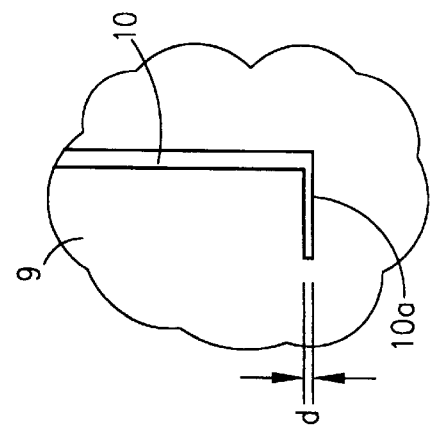

FIG. 9c, slot 10a is configured as a C-shaped slot, where a first end of the C-shaped slot intersects slot 10 at point 12, and a second end 10d lies in line with slot 10. The end of slot 10 is separated from the second end of slot 10a by tab 24. The C-shaped configuration of slot 10a operates in the following manner. Hub 2 is moved forward within the container until pin 7 reaches end 12 of slot 10. At this point, the needle is rotated by pushing pin 7 along slot 10a until it reaches end 10d. At this point, ping 16 biases the hub 2 away from ridge 15, pressing pin 7 against tab 24. Tab 24 acts as a stop, preventing spring 16 from decompressing further and causing needle 1 to retract into the container. Additionally, slot 10a may be designed so as to be narrower than the diameter d of pin 7 (FIG. 9d), so that it grips pin 7 when pin 7 is forced into slot 10a. Also, slot 10a may be a straight slot having a tooth 10e on one or both sides (FIG. 9e), where tooth 10c causes the width of the slot to narrow to less than the diameter of pin 7 at a specific point. When pin 7 is forced into slot 10a, it snaps into position. Also, a U-shaped bend 10f may interrupt slot 10a, making it difficult for pin 7 to accidentally leave slot 10a (FIG. 9f). If present, slot 10b may also be a straight slot, or it may also have any of the configurations shown in FIGS. 9a through 9f.

Figure 5:
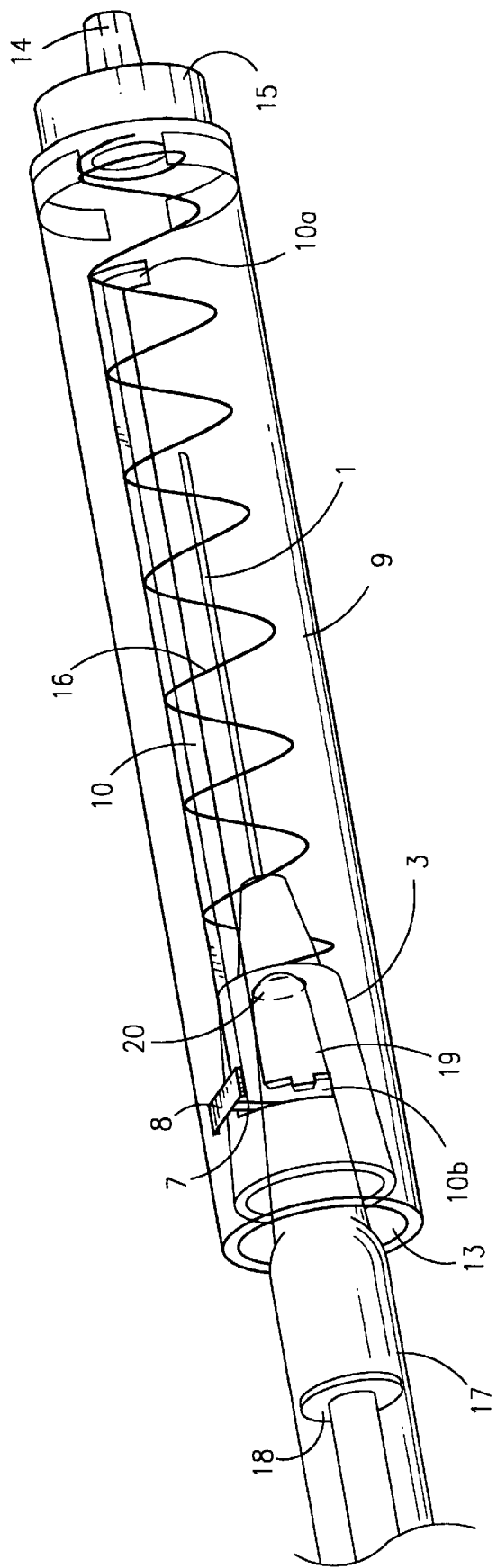
FIGS. 5 and 6 illustrate use of a syringe assembly with the safety needle of FIG. 3.
Figure 6:
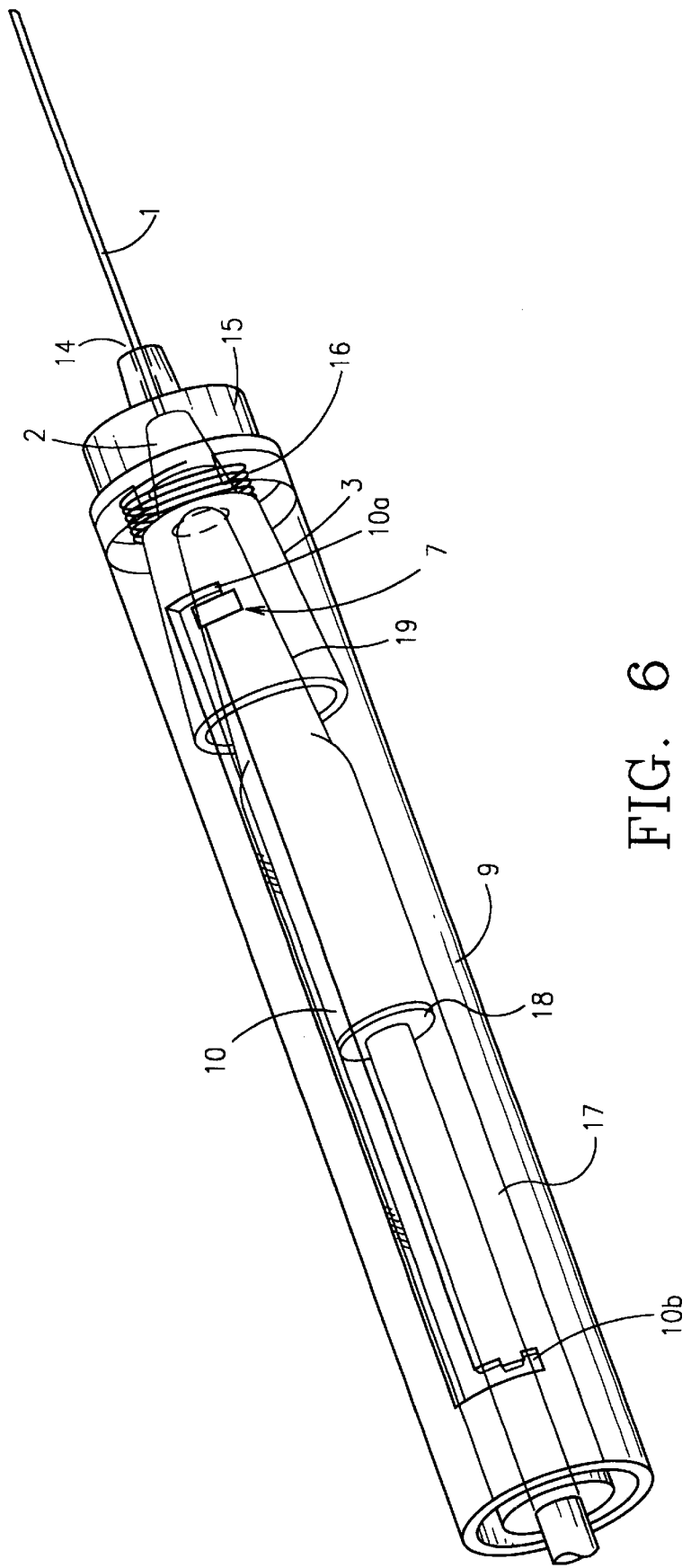

FIGS. 5 and 6 illustrate use of a syringe assembly with the safety needle of FIG. 3. The syringe comprises a syringe barrel 17, and a syringe plunger 18 slidably mounted therein Barrel 17 has a frustoconical tip 19 adapted to enter cavity 6 of sleeve 19 (cavity 6 is not shown in FIGS. 5 and 6, as it is occupied by tip 19.). Tip 19, after insertion into cavity 6, fictionally engages the interior of sleeve 3, forming a leakproof seal. A hole in tip 19 receives fluids which have passed through the bore of needle 1.

As shown in FIG. 6, syringe barrel 17 may be used to push the needle assembly within the container toward the second end of the container, compressing the spring and causing needle 1 to emerge through hole 14. In this position, the container encases at least a portion of barrel 17. Barrel 17 may then be rotated, causing sleeve 3 to rotate. This causes pin 7 to enter slot 10a, locking the syringe needle into position. The assembled syringe, with the needle exposed, may then be used to take a sample of a fluid. More particularly, the assembled syringe may be used to administer an injection to a patient, or to take a sample of arterial or venous blood from a patient.

After use, the contaminated needle may be discarded by rotating barrel 17 in the reverse direction to free pin 7 from slot 10a. This allows spring 16 to decompress, causing the container to s forward off of the syringe barrel and cover needle 1. The syringe barrel may then be separated from sleeve 3. A cap (not shown in the figures) is then placed over the opening at each end of the container. The container with the needle concealed therein may then be discarded with minimal risk of injury from contact with the contaminated needle. The syringe barrel and plunger may be discarded, or sterilized in an autoclave for reuse.

If desired, the interior diameter of the container may narrow from a diameter which is great enough to receive the syringe barrel to a diameter which is little greater than the diameter of needle 1. This narrowing occurs at a point at or near the second end of the container. When the needle is withdrawn into the container, the pointed end of the needle then occupies a position where the container diameter is small. This helps prevent the needle point from moving away from the axis of the container.

One difficulty in manufacturing an article of this type lies in the difficulty in getting the pin on the needle assembly to properly engage slot 10. For example, the invention of D'Amico (vide supra) presents a substantially cylindrical hub having a radially protruding pin attached thereto positioned within a tubular container. The inner circumference of the container is substantially the same as the outer circumference of the hub. The pin is positioned within a slot in the wall of the container, where each end of the slot is closed. However, this article is difficult to manufacture inexpensively. When the hub slides into the container, the radially protruding pin is blocked by the end of the tubular container wall, and cannot readily enter the container.

Figure 27A:
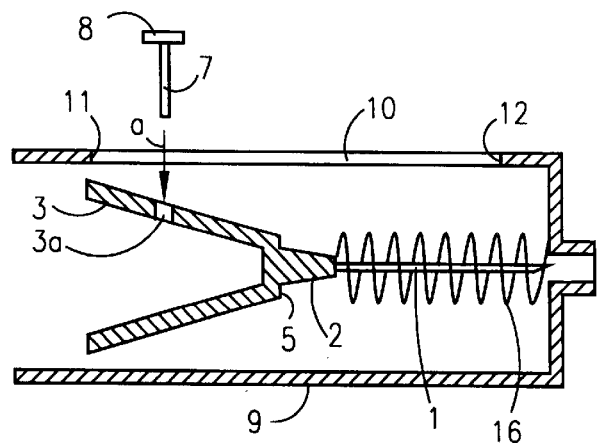
FIG. 27*a* shows a method for assembling the hypodermic needle of FIG. 3*a*.

This invention attempts to solve this problem. When the container is manufactured in one piece, the combination of pin 7 and crosspiece 8 will not pass through slot 10 when the needle assembly of FIG. 1 is positioned inside the container of FIG. 2. To overcome this difficulty, one can position the needle assembly inside the container prior to attaching pin 7, and then insert pin 7 through slot 10 in the direction of arrow a into a hole 3a in sleeve 3 and secure the pin to sleeve 3, as shown in FIG. 27. The pin may be connected with the annular sleeve by means of an adhesive. Alternatively, the pin is connected with the annular sleeve by screwing a treaded male joint on the pin into hole 3a, where hole 3a is a threaded female joint on the sleeve 3. If extra security is desired, pin 7 may be connected with the sleeve 3 by applying an adhesive to either of the threaded male joint or the threaded female joint on the sleeve 3 (or both of the threaded joints), screwing the threaded male joint into the threaded female joint on the sleeve, and allowing the adhesive to bond the male joint to the female joint.

Figure 7:
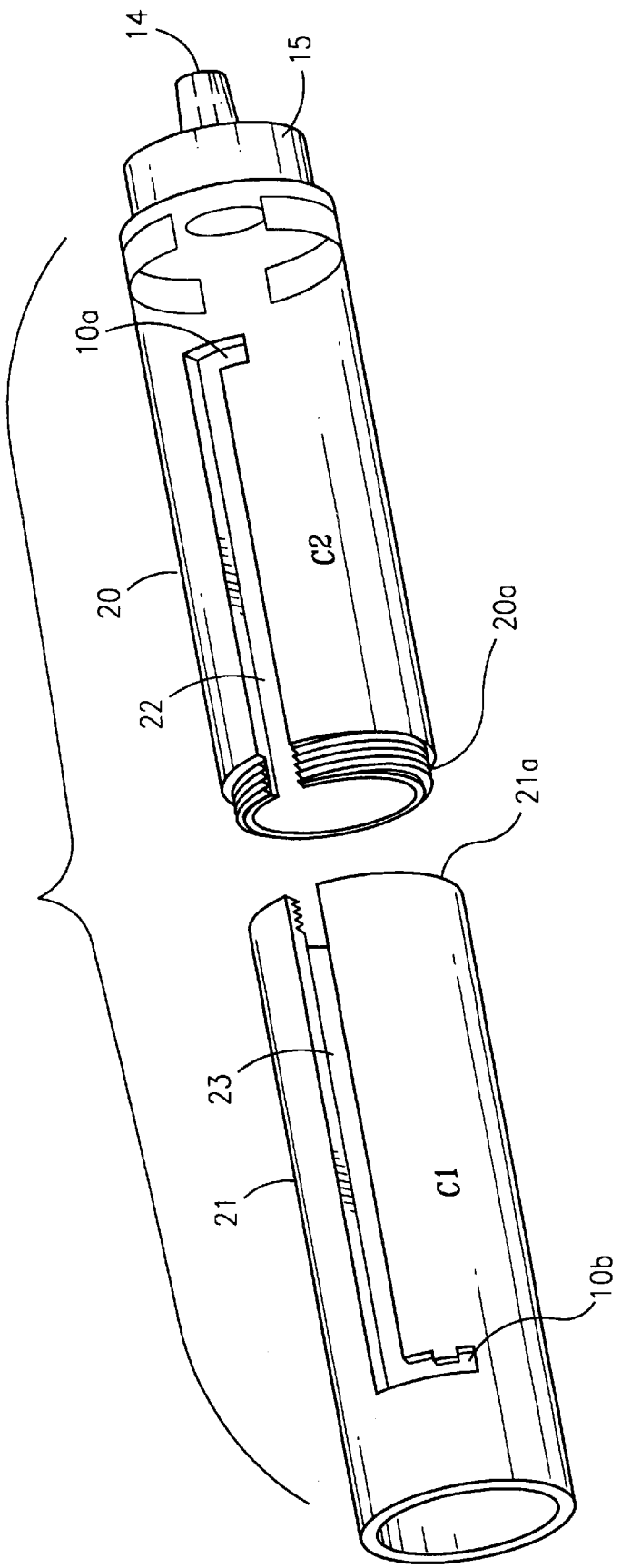
FIG. 7 illustrates the parts used to form the container of FIG. 2.

A second, and more preferred, method of solving the problem involves formation of the container in two parts, as shown in FIG. 7. The container is formed from an anterior portion 20 and a posterior portion 21. Anterior portion 20 has a first open end adapted to receive a syringe barrel and a second open end adapted to receive a hypodermic needle. Ridge 15 is positioned on the interior surface of the wall of anterior container portion 20. A first longitudinal slot 22 runs from the first end of the anterior portion of the container to point 12, near the second end of the anterior portion of the container. Slot 10a meets slot 22 at a right angle. Posterior portion 21 of the container has a first open end adapted to receive a syringe barrel and a second open end adapted to receive a syringe barrel. A second longitudinal slot 23 runs from the first end of the posterior portion of the container to point 11, near the second end of the posterior portion of the container. The first end of 20 and the first end of 21 are adapted to be joined together to form the complete container, by attaching 20 and 21 together so that slots 22 and 23 cooperate to form slot 10. The point of attachment between pieces 20 and 21 is shown in FIG. 2 as line 9a.

The manner in which 20 and 21 are joined together is not particularly limited. Parts 20 and 21 may be bonded together by means of a biocompatable adhesive. Alternatively, threaded ends on 20 and 21 may be screwed together, and then secured with a suitable adhesive. Also, a ridge on an interior surface of one piece may snap into a groove on an exterior surface of another piece. The ridge may be treated with an adhesive prior to snapping it into the groove. Finally, if 20 and 21 are made from a thermoplastic material (ie., polyolefin), they may be heat-sealed together. In the embodiment illustrated in FIG. 8, a threaded end 20a on container portion 20 is screwed onto a threaded end 21a on container portion 21.

Figure 8:
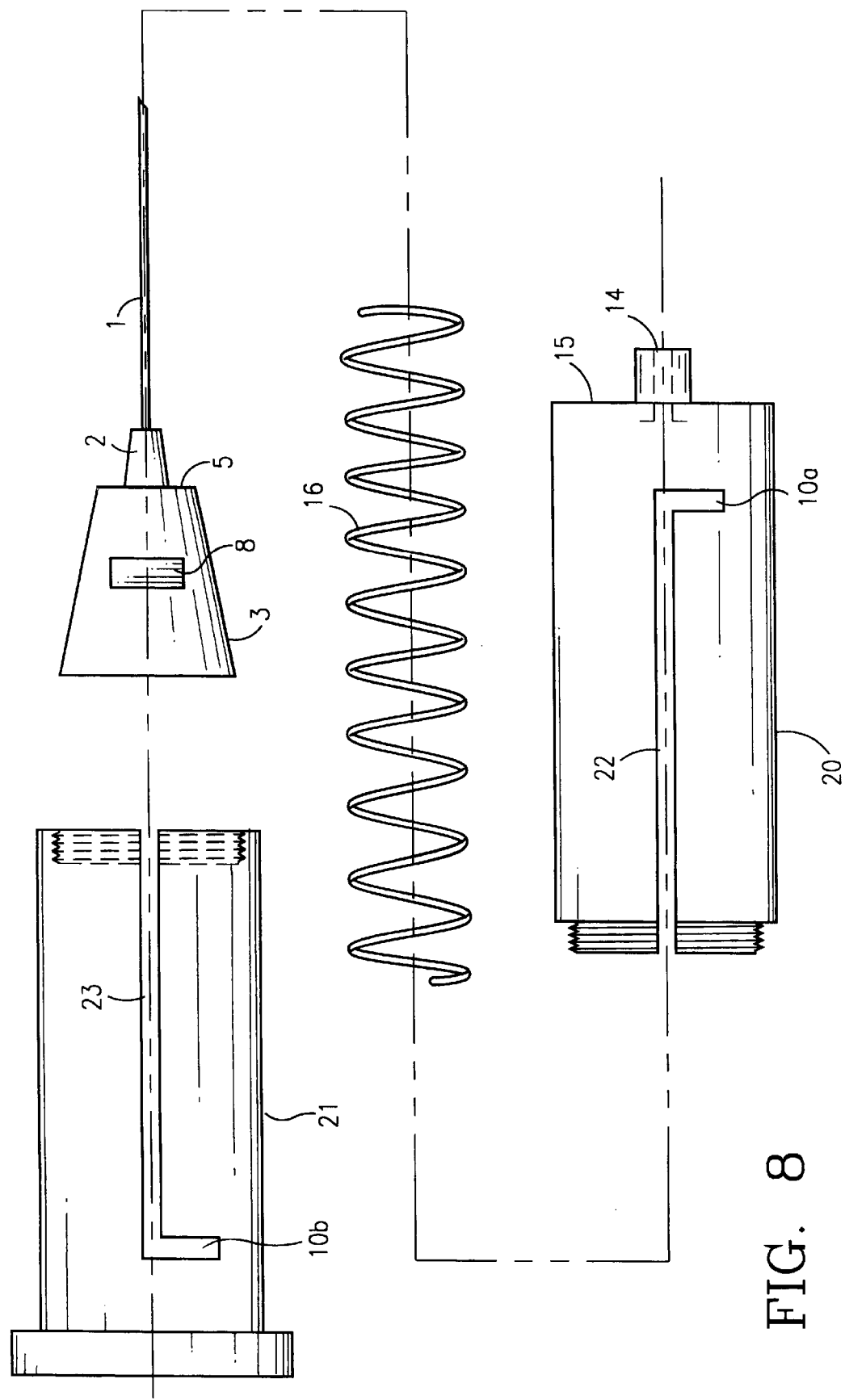
FIG. 8 is an exploded view of the retractable hypodermic safety needle within a container shown in FIG. 3.

The complete assembly is manufactured in the following manner, shown in FIG. 8. A spring 16 and the needle assembly are joined together by joining a first end of the spring to ridge 5 on hub 2. The needle 1 is positioned along the helical axis of the spring. This assembly is then positioned within the anterior portion 20 of the container so that a second end of the spring engages ridge 15. Container portion 20 is then joined to container portion 21 so that:

a) slots 22 and 23 lineup to form slot 10; and b) pin 7 is slidably engaged by slot 10.

Alternatively, hub 2 may be positioned within posterior portion 21 so that pin 7 engages slot 23, and then part 20 may be joined to part 21 container so that the second end of the spring engages ridge 15. Again, when joining pieces 20 and 21, care should be taken to ensure that slots 22 and 23 are aligned so as to form a single slot 10 which engages pin 7.

This assembly method allows the safety needle to be assembled quickly and easily, and avoids the difficulty of trying to position the needle inside a fully assembled container without damaging the pin by forcing it past the rim of the container.

In another embodiment, the container is manufactured in one piece, as shown in FIGS. 28a and 28b. The container is a tubular structure having an opening at each end. The first end of the container has an opening 13 adapted to receive a syringe barrel, and the second end of the container has an opening 14 which is sufficiently large to receive the hypodermic needle, but too small to receive a syringe barrel. The longitudinal slit 10 in the wall of the container is open at one end, having an open end 10d extending to the first end of the container, and a closed end near the second end of the container. The container is provided with a mechanism for preventing the pin which slidably engages the slit from passing through the open end of the slit.

The mechanism for preventing the pin 7 from passing through the open end of the slot may be a non-elastic ring 64 which is rigidly secured to the exterior surface of the first end of the container. The non-elastic ring is designed to slide over the exterior surface of the first end of the tubular container, as shown in FIG. 28a, and then be rigidly secured to the exterior surface of the first end of the container, preferably by means of an adhesive. The ring blocks efforts to force the pin from passing through the open end of the open end of the longitudinal slot. Tabs 10d prevent the ring 64 from sliding too far onto the container and blocking access of pin 7 to slot 10b.

The mechanism for preventing the pin 7 from passing through the open end of the slot may also be a non-elastic trap 65 having a first end and a second end, where the first end of the strap is connected to the exterior surface of the first end of the container on one side of the open end 10d of the longitudinal slot 10, as shown in FIG. 28b. The strap should be sufficiently long to allow the second end of the strap to reach a position on the exterior surface of the first end of the container on the other side of the longitudinal slot. The second end of the strap is then secured to this position, as shown in the Figure. This may be done using velcro, or a snap, or a buckle.

In the event that hub 2 is significantly smaller than the container, the needle may wobble about the axis of the container. Methods of preventing this by anchoring the hub at a defined distance from the inner wall of the container will now be explored. As shown in FIG. 10, it is possible to secure two pins 7, each having a crosspiece 8 mounted thereto, on a single needle assembly, where the two pins are directed in opposite directions. Such a needle assembly may be mounted in a container having two slots 10a in opposite sides of wall 9. A transverse slot 10a intersects each slot 10, with each slot 10a running in the same direction (i.e., either clockwise or counterclockwise, when viewed from the second end of the container along the container axis). This version of the apparatus operates in the same manner as the assembled a of FIG. 3. The only difference is that the presence of the second pin anchors hub 2 of the needle assembly more firmly along the axis of the container (FIG. 11a). Another method of anchoring the hub along the container axis is to use a hub having a single pin 7 with two crosspieces 8 attached thereto. The two crosspieces are separated by a distance equal to the thickness of the container wall, with one crosspiece being outside the wall and the other crosspiece being inside the wall, fixing the hub at a defined distance tom the inner wall of the container (FIG. 11b). Finally, a shield 8a which is mounted to the outside of the container can cover the longitudinal slot, preventing crosspiece 8 from moving relative to the container axis (FIG. 11c). A portion of the crosspiece should be accessible from an open side 8b of the shield 8a.

Figure 12:
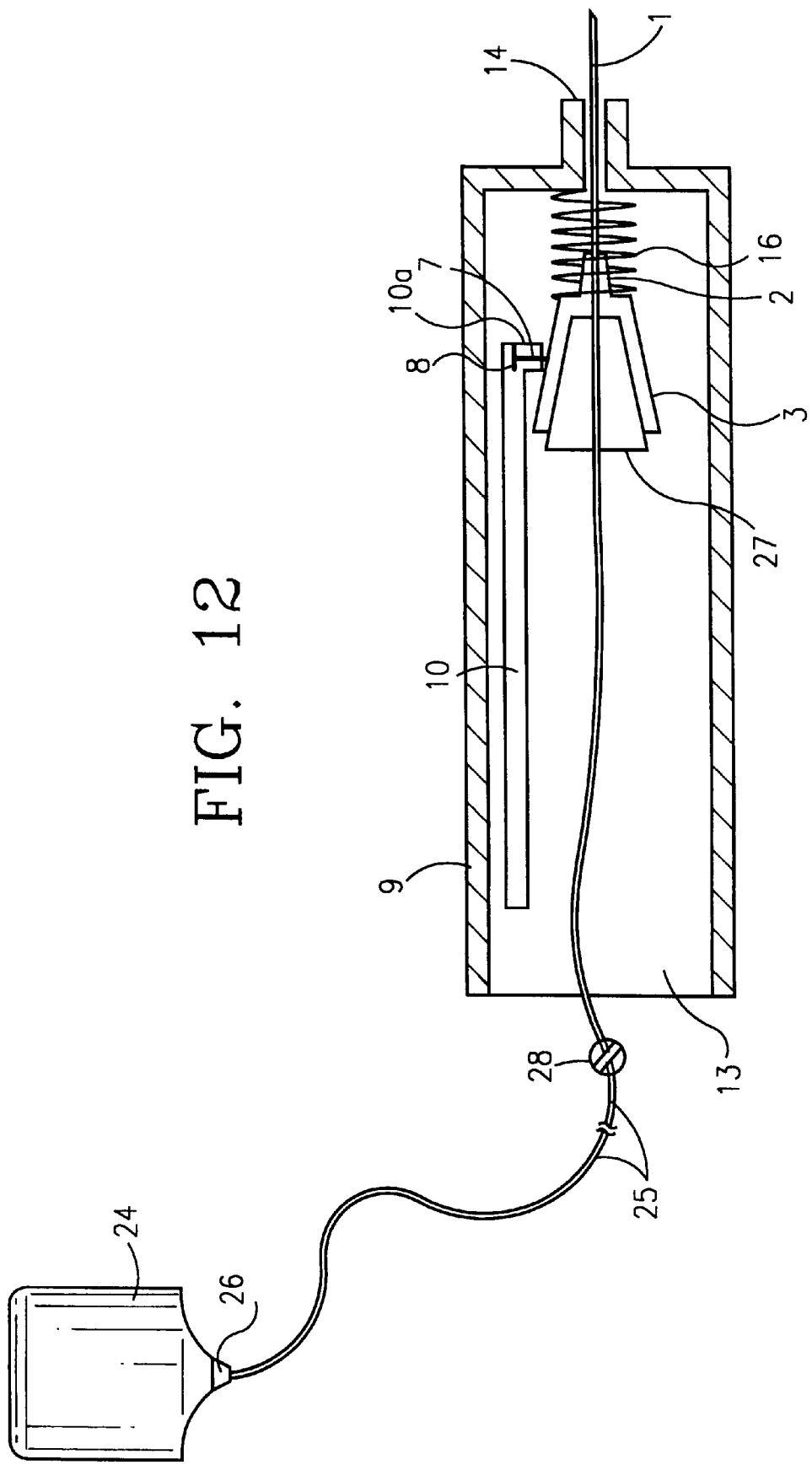
FIG. 12 shows an apparatus for administering a fluid intravenously.

The apparatus of FIG. 3 may also be used to administer fluids intravenously to a patient (FIG. 12). Needle 1 is exposed by sliding piece 8 forward toward need-receiving opening 14, carrying hub 2 toward the second end of the container until the needle passes through opening 14 and is exposed. Piece 8 is then pushed sideways until pin 7 enters slot 10a, locking the needle into the exposed position. An IV bag 24 or other container for fluids to be administered intravenously is obtained. A first end of a tube 25 is connected to an opening 26 in the bag. The second end of the tube features a frusto-conical male joint 27. The second end of the tube 25 is secured to the syringe needle assembly. This is done by frictionally securing the male joint 27 to the inner surface of the frusto-conical cavity 6 defined by annular sleeve 3. Needle 1 is inserted into a patient's vein. Liquid contained in the IV bag is allowed to flow out of the bag, through the tube, and into the patient's vein. This is normally done by elevating the IV bag relative to the syringe needle assembly. The tube may also have a valve 28 or other mechanism for controlling the rate at which fluid from the IV bag enters the patient's aim. When needle 1 is withdrawn from the patient's vein, piece 8 is then pushed sideways until pin 7 exits slot 10a, unlocking the needle. Sprig 16 then causes needle 1 to withdraw into the container.

FIG. 13 shows an alternative embodiment of the needle assembly of FIG. 1. This embodiment of the needle assembly features a hollow straight needle 29 having two ends. The needle 29 extends through a hub 30, so that a first end of the needle 29a points in a forward direction, and a second end of the needle 29b points in a reverse direction. Pin 7 is rigidly connected with said hub, and extends in a radial direction. Crosspiece 8 is connected with the pin at a defined distance from the hub. Preferably, a rubber sheath 31 covers end 29b of needle 1.

FIG. 14 shows the needle assembly of FIG. 13 mounted within the container of FIG. 2. Pin 7 is slidably engaged by the longitudinal slot 10, wit crosspiece 8 acting to support hub 30 so that it is positioned on the axis of the container. Needle end 29a is directed toward needle-receiving opening 14. End 29a of needle 29 is exposed by using the thumb or finger to manually slide piece 8 forward toward needle-receiving opening 14, carrying hub 30 toward the second end of the container until the needle end 29a passes through opening 14 and is exposed. Piece 8 is then pushed sideways until pin 7 enters slot 10a, locking the needle into the exposed position. The needle may then be inserted into a patient's blood vessel. The rubber sheath prevents the patient's blood from traveling through the needle.

Figure 15:
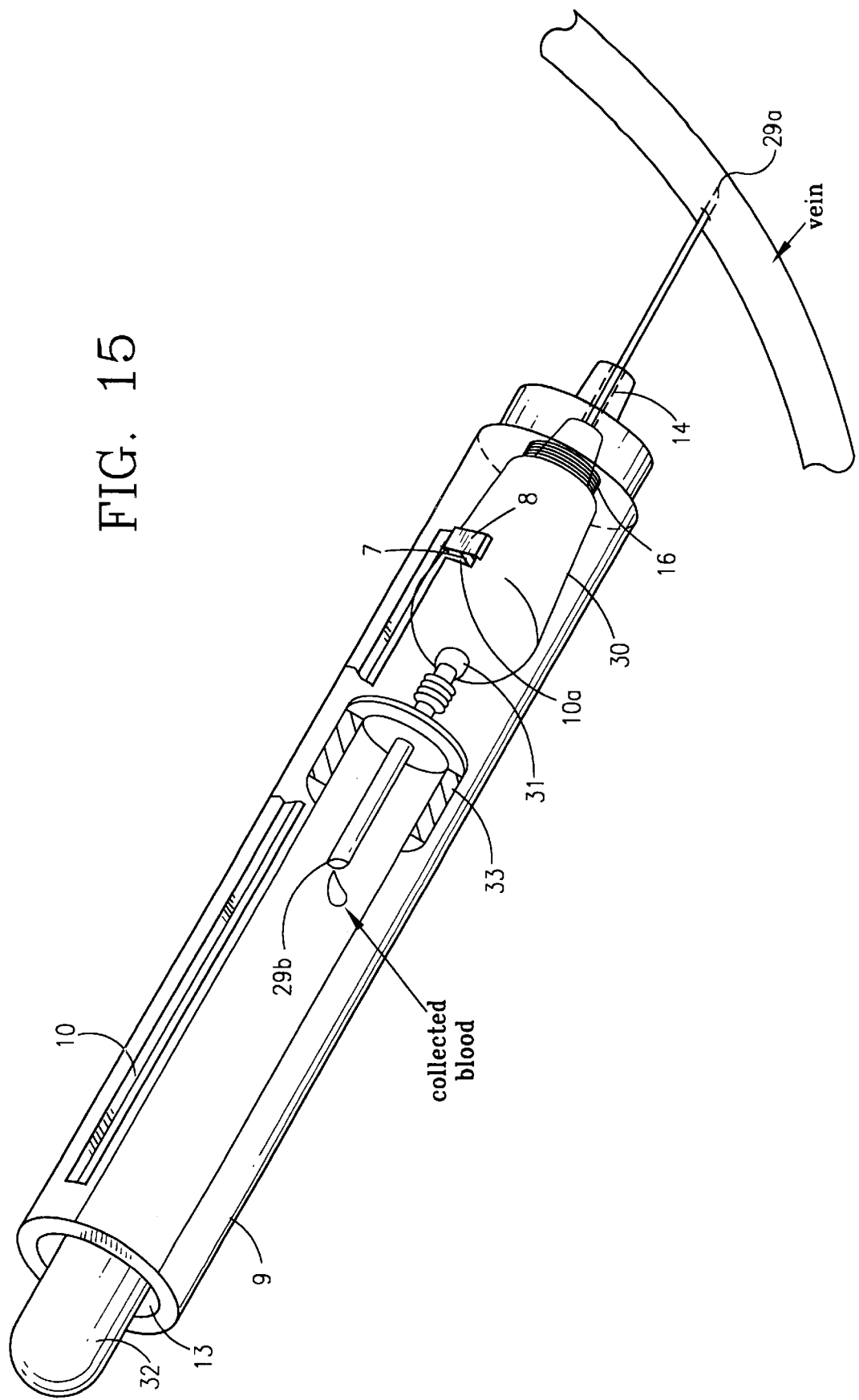
FIG. 15 shows the apparatus of FIG. 14 in use.

The assembly of FIG. 14 may be used with a receptacle for receiving a blood sample, as shown in FIG. 15. This receptacle is a test tube 32 having an open end. A rubber septum 33 seals the open end of the test tube. The interior of the test tube may be under vacuum. While needle 29 is in the patient's blood vessel, the end of the test tube which is sealed by septum 33 is inserted into opening 13 of the container until septum 33 contacts rubber sheath 31. The test tube is then pushed toward hub 30, and septum 33 pushes the end of rubber sheath 31 along needle 29 toward hub 30, exposing end 29b of needle 29. End 29b of needle 29 pierces the rubber sheath 31 and septum 33, entering the test tube. Blood from the patient then travels through hollow needle 29 into the test tube. After taking a sample of the patient's blood, test tube 32 is removed from the container. Rubber sheath 31 resumes its original configuration, covering end 29b of the needle and cutting off the flow of blood. Needle 29 is then withdrawn from the patient's blood vessel. Crosspiece 8 is then pushed sideways until pin 7 exits slot 10a, unlocking the needle. Spring 16 then causes needle 1 to withdraw into the container.

As in the syringe needle assembly of FIG. 3, piece 8 is sufficiently large that it cannot pass through slit 10 into the interior of the container, and is rigidly secured to a defined position along the length of pin 7, where the defined position on pin 7 is chosen so that hub 30 of the needle assembly is positioned along the cylindrical axis of the container. More particularly, the distance between the axis of hypodermic needle 1 and crosspiece 8 is equal to the one half the external diameter of the wall 9 of the container. This retains needle 29 along the axis of the container.

The use of crosspiece 8 to retain needle 1 in position is particularly important in an apparatus for obtaining blood samples. The container has to be wide enough to receive the test tube, which in turn is normally wider than hub 2. Without crosspiece 8, pin 7 would slip out of slot 10, and end 29b of needle 29 would fall against the inner surface of wall 9. Needle 29b would then be incorrectly positioned to penetrate septum 33.

It is important to note that the container having the longitudinal slot therein is structurally identical to the container of FIG. 2, regardless of whether it is intended to receive a syringe barrel, an IV tube, or a test tube for drawing a blood sample. The only significant difference is that the diameter of the container will vary depending on the size of the article which it is intended to receive.

Figure 16:
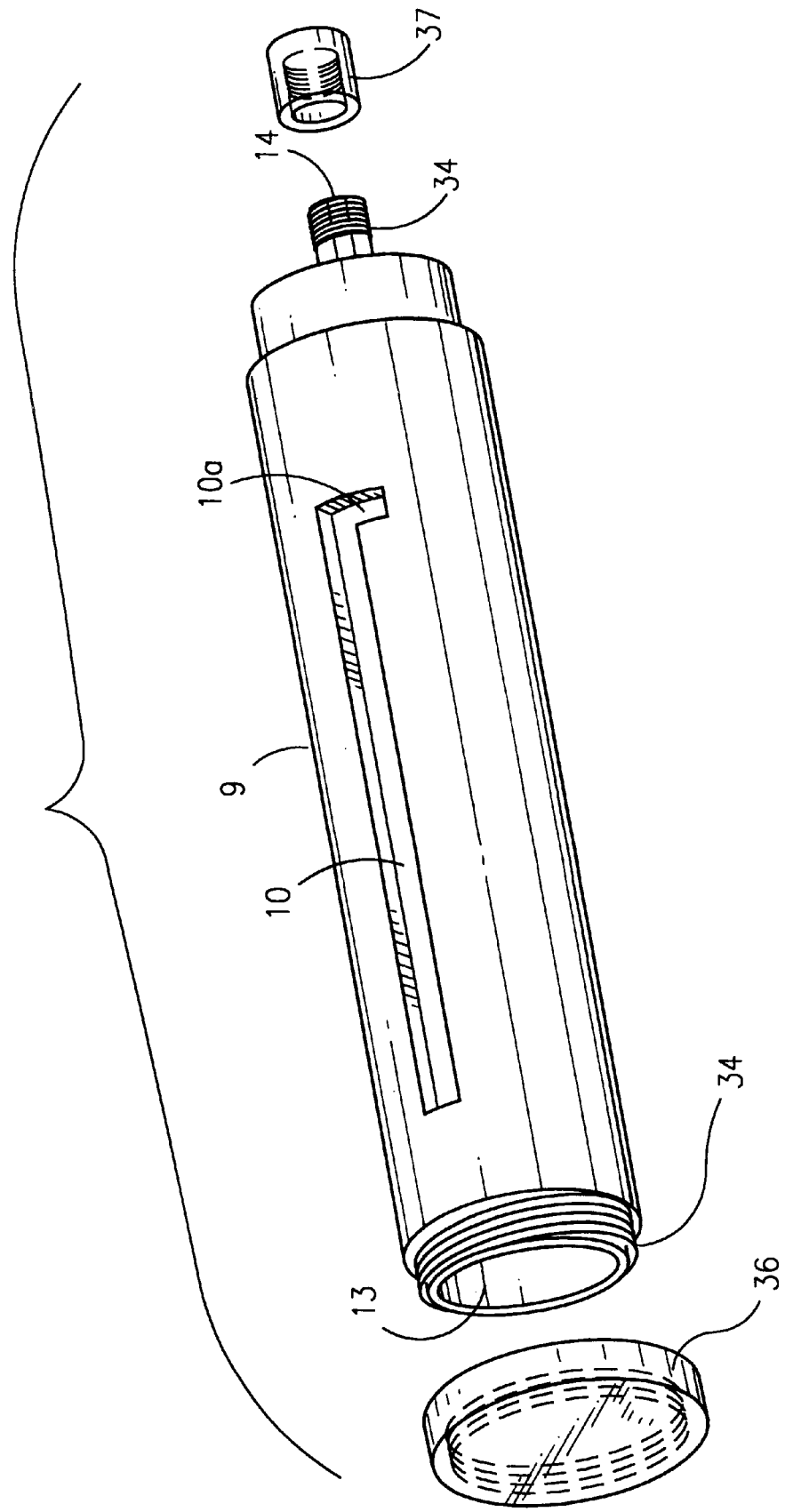
FIG. 16 shows the container of FIG. 2, having screw-on caps applied to each end.

As shown in FIG. 16 (note that the needle assembly has been omitted from FIG. 16 in the interests of clarity), a threaded male joint 34 may surround opening 13 at the first end of the container of FIG. 2, and a threaded male joint 35 may surround opening 14 at the second end of the container. Cap 36 having a threaded female joint may be screwed onto joint 34, covering opening 13, and cap 37 having a threaded female joint may be screwed onto joint 35, covering opening 14. This is normally done whenever the needle is not intended to be exposed, so as to minimize the risk of accidental contact with the tip of the needle.

Figure 17:
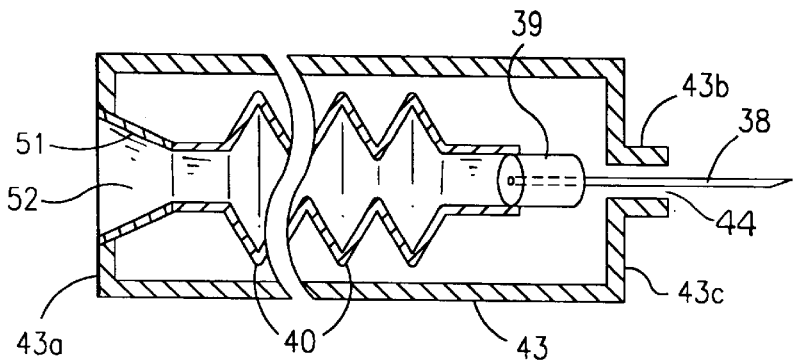
FIG. 17 shows a cross-sectional view of a second embodiment of the invention, where an adjustable length tube is adapted to connect a syringe to a hypodermic needle.

A second embodiment of the invention will now be discussed. The second embodiment of the retractable syringe needle features a hypodermic needle assembly similar to that shown in FIG. 1 for use in the first embodiment. The needle assembly, shown in FIG. 17, features a hollow hypodermic needle 38 and a cylindrical hub 39 having an axial passage through. The hollow needle is rigidly connected with the hub so that the axial passage and the interior of the hollow needle form a continuous conduit. Hub 39 is secured to one end of an adjustable-length tube 40 so that the interior of hollow needle 38 makes fluid contact with the interior of tube 40. Tube 40 is preferably impermeable to liquids, non-elastic, and axially collapsible. By collapsing the tube in an axial direction, the length of tube 40 may be changed from a first extended length to a second contracted length. The tube may then be extended in an axial direction, restoring the length of the tube to the first extended length.

A tubular sheath 43 is disposed around the adjustable-length tube 40. The tubular sheath 43 has a first end 43a which is rigidly connected with the first end of the adjustable length tube and a second end 43b having an opening 44 which is sufficiently large to allow the end of the hypodermic needle 38 to pass therethrough. Sheath end 43a is connected to tube 40 by means of a hollow conical member 51 having an inner surface defining a cavity 52 and an outer surface. The outer surface of member 51 is rigidly secured to end 43a of sheath 43. When the apparatus is not in use, the opening at each end of the tubular sheath may be covered by a cap (not shown in the drawings). The caps may screw onto the sheath, or snap onto the sheath.

Figure 18A:
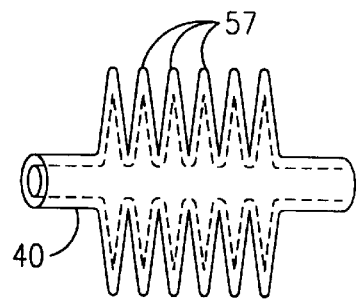
FIGS. 18*a* and 18*b* show a first adjustable-length tube for use with the embodiment of FIG. 17.
Figure 18B:
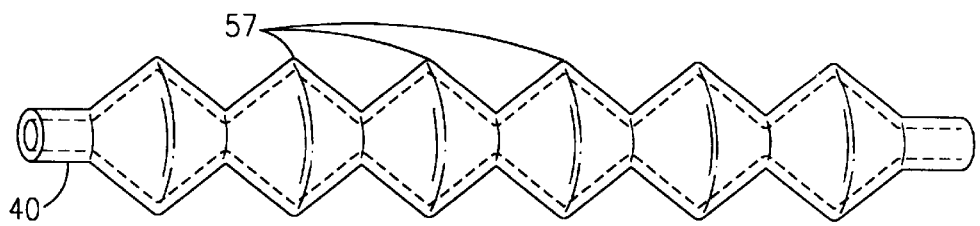

The preferred embodiments of the adjustable-length tube 40 will now be discussed. The most preferred type of adjustable-length tube 40 contemplated for use in this invention features a series of circumferential pleats 57 disposed along the length of the tube, as shown in FIGS. 18a and 18b. When tube 40 is in its contracted or collapsed state (FIG. 18a), pleats 57 are folded together. The adjustable-length tube may be lengthened by pulling one end of tube 40 (the end to which the hub is attached) away from the other, causing pleats 57 to unfold (FIG. 18b).

Figure 19A:
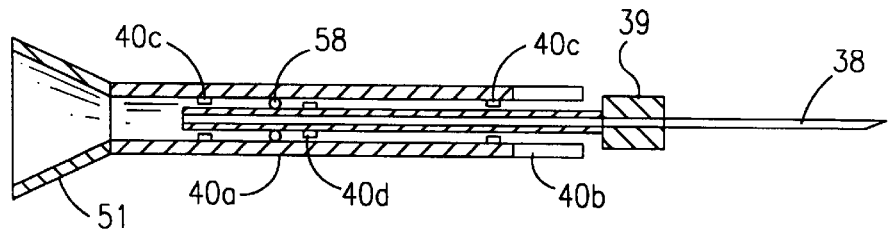
FIGS. 19*a* and 19*b* show a second adjustable-length tube for use with the embodiment of FIG. 17.
Figure 19B:
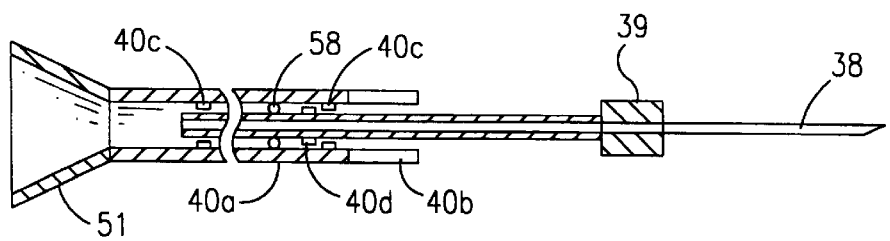

Another embodiment of adjustable-length tube 40 is a telescoping tube made from an outer tube 40a and an inner tube 40b, as shown in FIGS. 19a and 19b. The inner tube is slidably disposed within the outer tube. A first end of outer tube 40a is adapted to be secured to syringe barrel 40 through conical member 51, as previously described. A first end of inner tube 40b is adapted to be secured to hub 39. The inner tube 40b may be moved from a position where tube 40b is entirely or primarily disposed within tube 40a FIG. 19a), contacting tube 40, to a position where tube 40b is mostly exposed (FIG. 19b), expanding tube 40. Ridges 40c on the interior of outer tube 40a interact with a ridge 40d on the outer surface of tube 40b, acing as stops to prevent removal of tube 40b from tube 40a. Preferably, a leakproof sealing material 58 is disposed between the outer surface of the inner tube and the inner surface of the outer tube. This sealing material may be a hydrophobic, biocompatable polymer with a low coefficient of friction, such as silicone or teflon.

Figure 20A:
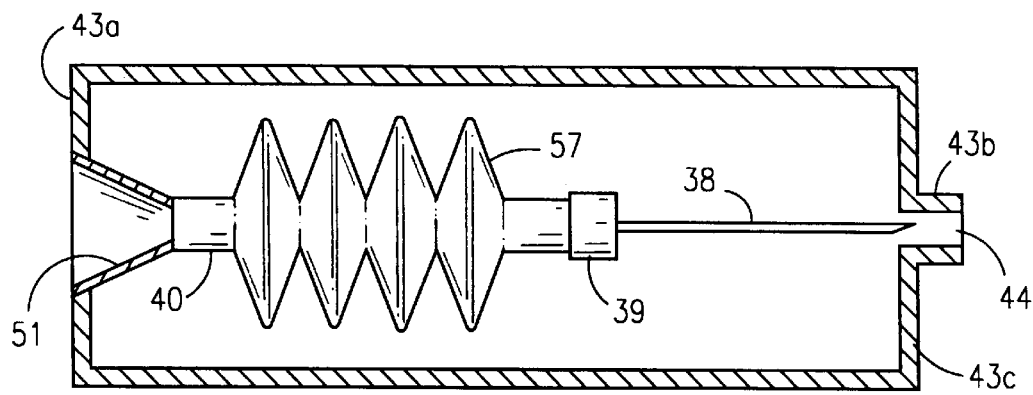
FIGS. 20*a* and 20*b* show the apparatus of FIG. 17 with the adjustable-length tube in a first, contracted state (FIG. 20*a*), and in a second, extended state (FIG. 20*b*).
Figure 20B:
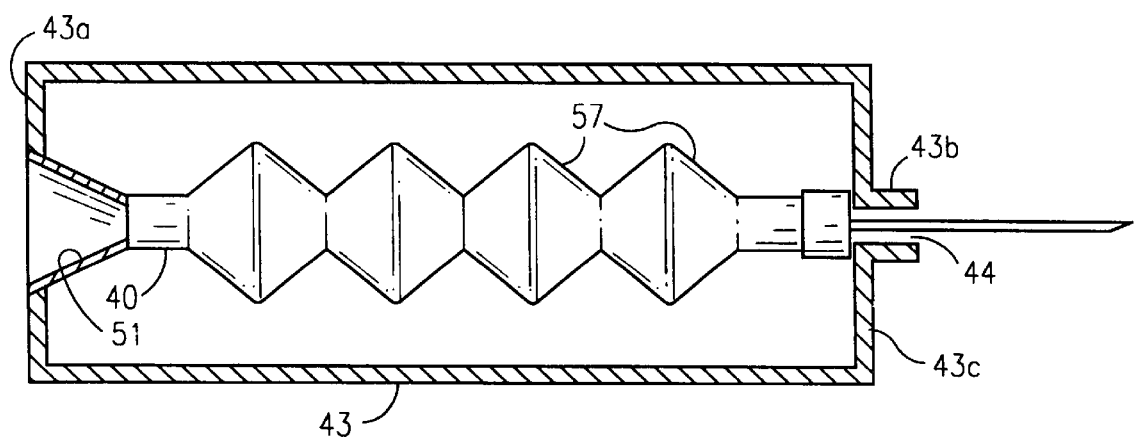

When the adjustable-length tube is contacted, the hypodermic needle is entirely disposed within the sheath (FIG. 20a). When the adjustable-length tube is extended, the end of the hypodermic needle is exposed through opening 44 in the second end of the sheath. If desired, the interior diameter of the sheath 43 may narrow from a diameter which is great enough to receive the adjustable-length tube 40 to a diameter which is little greater than the diameter of needle 1. This narrowing occurs at a point 43c near the opening 44. When the needle is disposed within the sheath, the pointed end of the needle then occupies a position where the inner diameter of the container is small (FIG. 20a). This helps prevent the needle point from moving away from the axis of the container.

Figure 21:
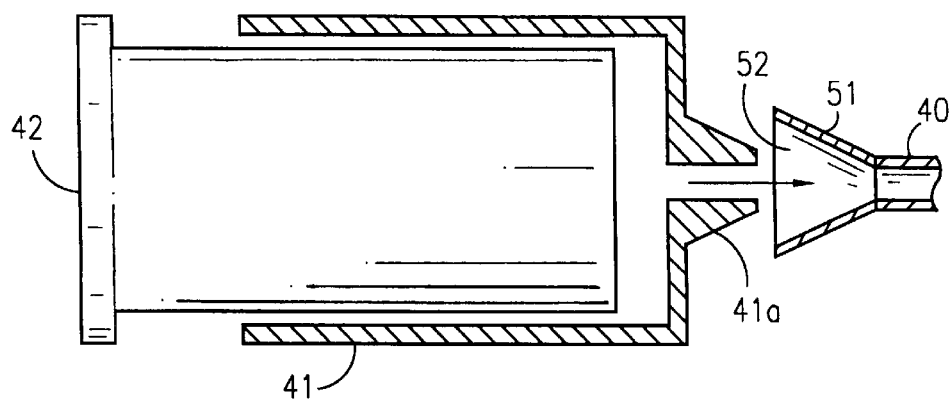
FIG. 21 illustrates how a syringe barrel may be coupled to the adjustable-length tube in the apparatus of FIG. 17.

A syringe barrel 41 having a plunger 42 slidably mounted therein may be reversibly secured to the other end of the adjustable-length tube 40 so that the interior of the syringe barrel is in fluid contact with the interior of the adjustable-length tube, as shown in FIG. 21. By raising the plunger and creating a partial vacuum within barrel 41, fluids may then be drawn through needle 38 (not shown in FIG. 21) and tube 40 into barrel 41. The syringe barrel 41 is secured to the first end of the adjustable-length tube 40 by means of hollow conical member 51. The inner surface of member 51 defines a frustoconical cavity 52 adapted to frictionally engage a frustoconical tip 41a of the syringe barrel. The conical member 51 has a narrow end with a passage 51a therethrough. The narrow end of member 51 is connected to the end of the adjustable-length tube 40 to which hub 39 is not secured The frustoconical 52 cavity makes fluid contact with the interior of the adjustable-lengthen tube 40 through the passage 51. As the outer surface of member 51 is rigidly secured to the first end of the tubular sheath 43 (sheath 43 is not shown in FIG. 21), sheath 43 is immobile relative to a syringe barrel 41 connected to tube 40.

Figure 22A:
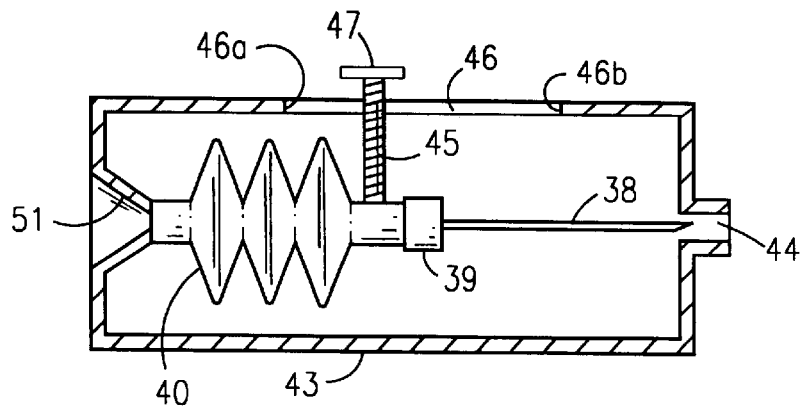
FIGS. 22*a*, 23, and 23*a* illustrates a mechanism for manually adjusting the length of the adjustable-length tube.
Figure 27B:
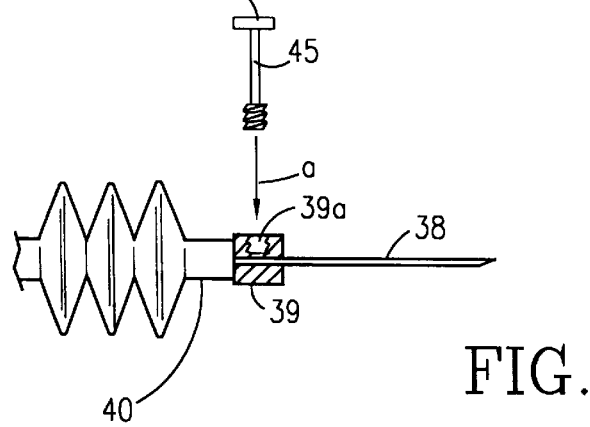
FIG. 27*b* shows a method of connecting a knob to an adjustable-length tube to produce a tube as used in the apparatus of FIG. 22.

The second embodiment of the invention additionally features a mechanism allowing the user to reversibly alter the length of the adjustable-length tube from the contracted length to the extended length at will. This mechanism features a knob 45 which is rigidly connected with hub 39, as shown in FIG. 22. The knob 45 may be indirectly connected to hub 39 by connecting knob 45 to the end of tube 40 to which hub 39 is attached, as in FIG. 22, or it may be directly attached to hub 39. The knob 45 may be connected with the hub 39 by inserting the end of the knob into a hole 39a in the hub, and securing the knob into position by means of an adhesive, as shown in FIG. 27b. Alternatively, the knob is connected with the hub by screwing a Headed male joint on the knob into bole 39a, where hole 39a is a threaded female joint on the hub 39. If extra security is desired, knob 45 may be connected with the hub by applying an adhesive to either of the threaded male joint or the threaded female joint (or both of the threaded joints), screwing the threaded male joint into the threaded female joint on the hub, and allowing the adhesive to bond the male joint to the female joint Similar methods may be used to secure the knob to the end of tube 40.

The knob 39 slidably engages a longitudinal slot 46 running along the length of the tubular sheath 43. Preferably, slot 46 is closed at both ends. Thumbrest 47 is accessible from outside sheath 43, and may be used to reversibly slide the knob from a first position 46a along the length of the longitudinal slot to a second position 46b along the length of the longitudinal slot, nearer opening 44 than the first position. When the knob is in the first position, the adjustable-length tube is contracted and the needle 38 is concealed within sheath 43. Sliding the knob into the second position causes the adjustable-length tube to extend, allowing the needle 38 to emerge through opening 44 in sheath 43. When the tube is contacted and the needle is concealed, caps may be used to cover the openings in the ends of the tubes.

Figure 23:
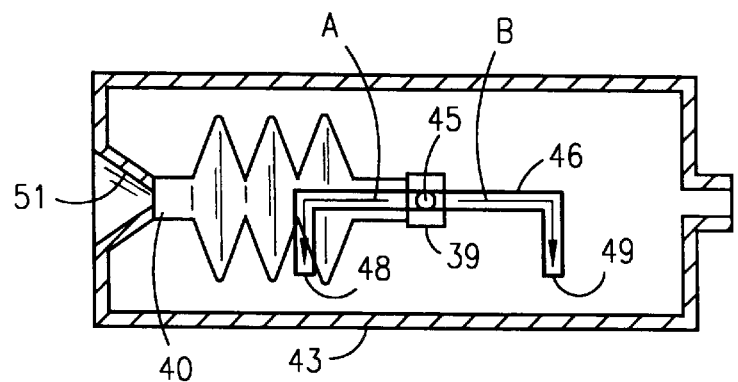
Figure 23A:
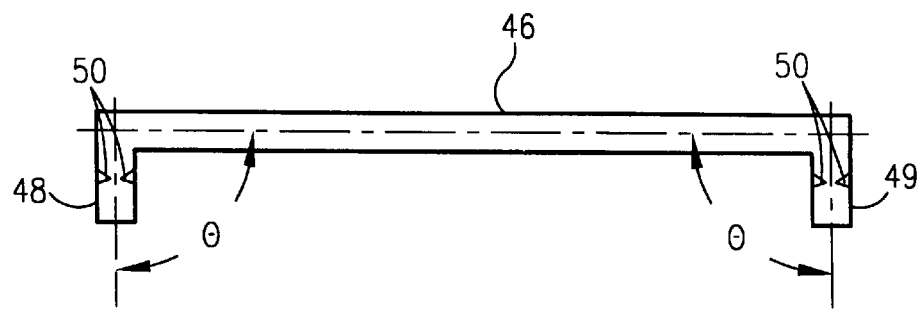

The knob may be reversibly secured at the first position along the length of the longitudinal slot 46, maintaining tube 40 in a contracted state. This may be done by sliding knob 45 into a second slot 48 which intersects the longitudinal slot at the first position, as shown by arrow "A" of FIG. 23 (For reasons of clarity, thumbrest 47 and needle 38 are omitted from FIG. 23.). Similarly, the knob may be reversibly securing at the second position along the length of the longitudinal slot 46, when tube 40 is extended, by sliding knob 45 into a third slot 49 which intersects the longitudinal slot at the second position, as shown by arrow B. Slots 48 and 49 are each wide enough to receive knob 45 readily. Preferably, slots 48 and 49 intersect slot 46 at an angle θ of 90° or less, shown in FIG. 23a If desired, slots 48 and 49 may be straight, or may have any of the configurations disclosed as usable for slots 10a and 10b, illustrated in FIG. 9a through 9f. Also, teeth or prongs 50 on the sides of slots 48 and 49 may be used to narrow the openings of slots 48 and 49 to slightly less than the width of the knob, so that the knob snaps into place when it is moved into one of slots 48 and 49. This prevents the knob from accidentally sliding into or out of a slot.

In a slightly different embodiment of the tubular sheath, shown in FIG. 29, the longitudinal slot has a first open end 46a extending to the end of the tubular sheath which is connected to the adjustable-length tube, and a second closed end 46b near the end of the tubular sheath which has the opening adapted to receive the hypodermic needle. The knob engaging the slot is prevented from passing through the open end of the slot by hollow conical member 51, which is rigidly secured to the inner surface of the sheath The assembly may be manufactured by sliding the hub having the pin connected thereto into the sheath so that the knob slides into the open end of the slot. The adjustable-length tube is connected to the hub at on end, and to conical member 51 at the other. The adjustable-length tube slides into the sheath, and member 51 is then secured to the inner surface of the sheath, as shown in FIG. 29 (Tube 40, hub 39, and the knob 45 have been omitted for clarity.

The hub 39 may be secured to one end of the adjustable-length tube 40 in the following manner. A male joint 53 is provided on one end of the hub, opposing needle 38. A female joint 54 is provided on one end of the tube 40. The male joint on the hub is then secured to the female joint on tube 40 so as to provide a leakproof seal, as shown in the exploded view of FIG. 24. One way of doing this is to provide a threaded male joint on the hub, and a threaded female joint on the adjustable-length tube, as shown in the figure. The male and female joints may then be screwed together. Alternatively, a waterproof and biocompatible adhesive material may be used to secure the female joint to the male joint.

A female joint 54a on the other end of tube 40 is secured to a male joint 53a on the narrow end of conical, syringe-receiving member 51. The method of doing this is not particularly limited. The end of part 40 may be adhesively bonded to the outer surface of part 51. Also, a treaded male joint on the outer surface of part 51 may be screwed into a threaded female joint on the inner surface of part 61.

Figure 24:
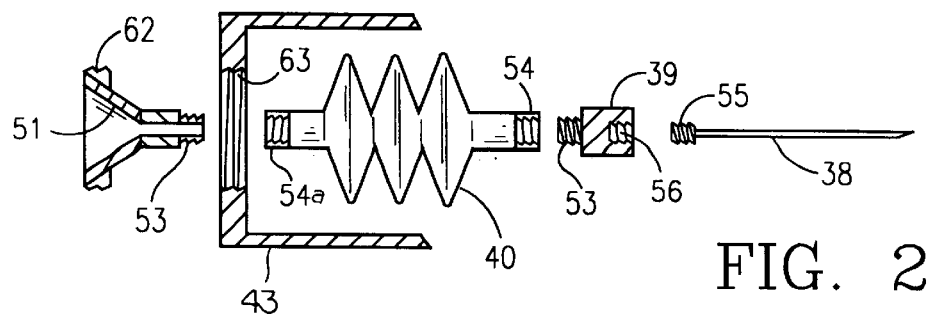
FIG. 24 provides an exploded view showing how the apparatus of FIG. 17 may be assembled.

Similarly, needle 38 may be secured to hub 39 by providing a male joint 55 on one end of the needle 38 (also shown in FIG. 24). A female joint 56 is provided on the hub, opposing the male joint 53 for attachment to tube 40. The female joint on the hub is then secured to the male joint on needle 38 so as to provide a leakproof seal. One way of doing this is to provide a threaded female joint 56 on the hub, and a threaded male joint 55 on the needle, as in FIG. 24. Joints 55 and 56 may then be screwed together. Alternatively, a waterproof and bioconpatible adhesive material may be used to secure the female joint 56 to the male joint 55. An additional possibility is that the hub may be molded around the needle 38.

The first open end 43a of tubular sheath 43 is secured to conical, syringe-receiving member 51 (FIG. 24). The method of doing this is not particularly limited. The open end 43a of part 43 may be adhesively bonded to the outer surftce of part 51. Also, a threaded male joint 62 on the broad end of the outer surface of part 51 may be screwed into a threaded female joint 63 on the inner suds of part 43 (see FIG. 24).

Figure 25:
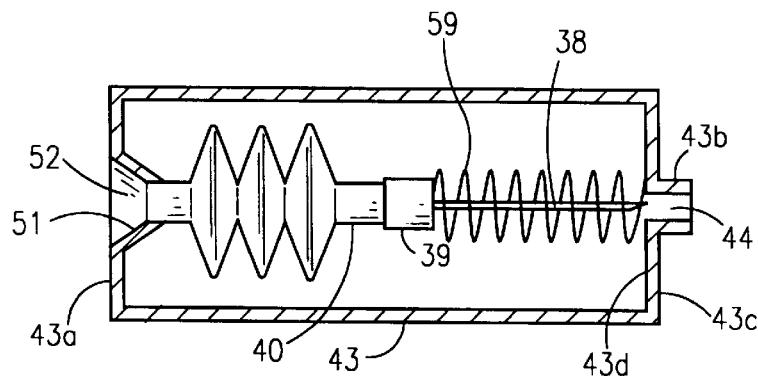
FIG. 25 shows a mechanism for biasing the adjustable-length tube into a contracted state.

A mechanism to bias the hub away from opening 44 in the second end of the tubular sheath, causing the adjustable-length tube to be compressed, may be added to the syringe needle assembly. Preferably, the biasing mechanism is a spring 59 having a first end which contacts the hub, and a second end which contacts a circumferential ridge 43d on the inner surface of the second end of the tubular sheath, as shown in FIG. 25. The force exerted on the hub by the spring may be readily overcome by using thumbrest 47 (not shown in FIG. 25) to push hub 39 toward sheath opening 44. The adjustable-length tube used with the biasing mechanism may be either a pleated or corrugated tube, or a telescoping tube.

Figure 26:
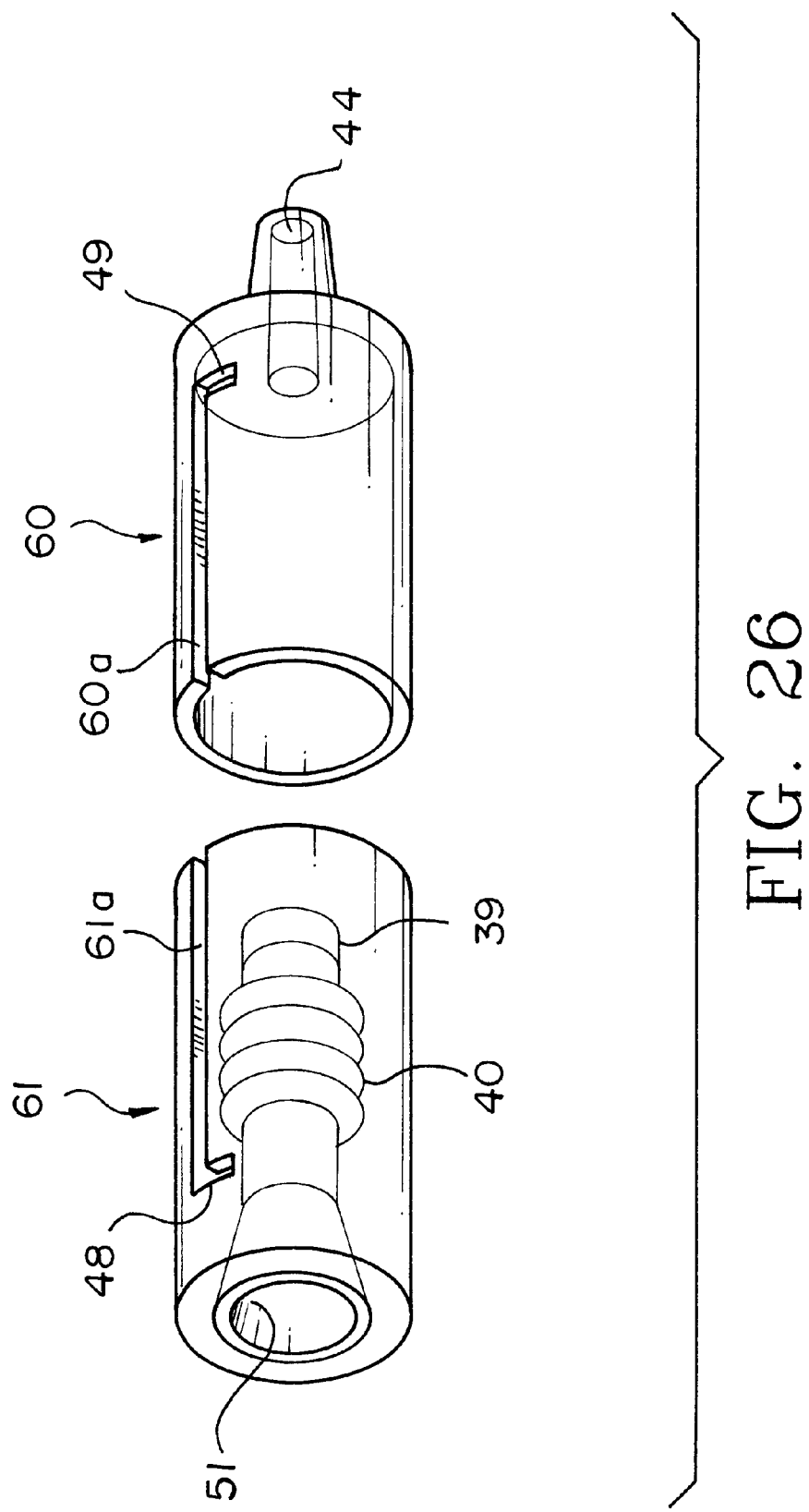
FIG. 26 provides a second exploded view showing how the apparatus of FIG. 17 may be assembled.

The tubular sheath used in making the retractable syringe needle may be made in the same manner as the container used for the first embodiment of the invention (see exploded view of FIG. 26). The sheath is made from an anterior tubular sheath portion 60 having a first open end, and a second open end having an opening 44; and a posterior tubular sheath portion 61 having a first open end adapted to be rigidly connected with the first end of the adjustable-length tube, and a second open end. A longitudinal slot 60a runs from the first end of anterior portion 60 toward the second end of portion 60. Similarly, a longitudinal slot 61a runs from the second end of posterior portion 61 toward the first end of portion 61. One end of tube 40 is secured to hub 39 having a needle 38 attached thereto (needle 38 is not shown in FIG. 26), and the other end of tube 40 is rigidly secured to the first end of posterior portion 61 through conical member 51 so that posterior portion 61 is disposed around tube 40. The first open end of the anterior portion is then rigidly fastened to the second open end of the posterior portion to form a continuous tubular structure (sheath 43). The end of needle 38 passes through opening 44 when tube 40 is elongated. When tube 40 is contracted, needle 38 is withdrawn into the tubular structure. Longitudinal slots 60a and 61a cooperate to form a continuous slot 46 running along the length of the sheath 43.

The manner in which 60 and 61 are joined together is not particularly limited. They be bonded together by means of a biocompatable adhesive. Alternatively, threaded ends on 60 and 61 may be screwed together, and then secured with a suitable adhesive. Also, a ridge on an interior surface of one piece may snap into a groove on an exterior surface of another piece. The ridge may be treated with an adhesive prior to snapping it into the groove. Finally, if 60 and 61 are made from a thermoplastic material (i.e., polyolefin), they may be heat-sealed together.

As described in the discussion of the first embodiment, the retractable needle of the second embodiment may be used to administer intravenous fluids. Instead of a syringe, a tube 24 having one end which is attached to an opening 26 in a container 25 of fluid to be administered intravenously and a second end having a male joint 27 connected thereto is connected to the needle assembly. This is done by reversibly securing the joint 27 to the first end of the adjustable-length tube so that the interior of the tube 24 is in fluid contact with the interior of the adjustable-length tube. The tube 24 is connected to the first end of the adjustable-length tube by fitting joint 27 into a female joint on hollow conical member 51. Member 51 has an inner surface which defines a cavity adapted to frictionally engage joint 27.

What is claimed is:

1. A retractable syringe needle, comprising:

a) a hollow hypodermic needle;

b) a cylindrical hub having an axial passage therethrough, said hollow needle being rigidly connected with the hub so that the axial passage and the interior of the hollow needle form a continuous conduit;

c) a adjustable-length tube having a first end and a second end, said tube having a length which may be reversibly altered from a first contracted length to a second extended length;

d) a means for reversibly securing a syringe barrel having a frustoconical tip to the first end of the adjustable-length tube so that the interior of the syringe barrel is in fluid contact with the interior of the adjustable-length tube;

e) a means for securing the cylindrical hub to the second end of the adjustable-length tube so that the interior of the hollow needle is in fluid contact with the interior of the adjustable-length tube;

f) a tubular sheath disposed around the adjustable-length tube; said tubular sheath having a first end which is rigidly connected with the first end of the adjustable-length tube and a second end having an opening which is sufficiently large to allow the end of the hypodermic needle to pass therethrough; and g) a means to reversibly alter the length of the adjustable-length tube from the contracted length to the extended length;

where the hypodermic needle is entirely disposed within the sheath when the adjustable-length tube is contracted, and where the end of the hypodermic needle is exposed through the opening in the second end of the when the adjustable-length tube is extended.

2. The retractable syringe needle of claim 1, wherein the means for securing the syringe barrel to the first end of the adjustable-length tube is a hollow conical member having an inner surface and an outer surface, said inner surface defining a frustoconical cavity adapted to frictionally engage the frustoconical tip of the syringe barrel and said outer surface being rigidly secured to the first end of the tubular sheath;

said conical member having a narrow end with a passage therethrough, said narrow end being connected to the first end of the adjustable-length tube so that the frustoconical cavity makes fluid contact with the interior of the adjustable-length tube through the passage in the narrow end of the conical member.

3. The retractable syringe needle of claim 1, wherein the means for securing the hub to the second end of the adjustable-length tube comprises a male joint on the hub, a female joint on the adjustable-length tube, and a means for securing the female joint to the male joint.

4. The retractable syringe needle of claim 3, wherein the means for securing the hub to the second end of the adjustable-length tube comprises a threaded male joint on the hub, and a threaded female joint on the adjustable-length tube; wherein said male joint and said female joint are adapted to be screwed together.

5. The retractable syringe needle of claim 3, wherein the means for securing the female joint to the male joint comprises an adhesive.

6. The retractable syringe needle of claim 1, wherein the adjustable-length tube is impermeable, non-elastic, and axially collapsible from said extended length to said contracted length.

7. The retractable syringe needle of claim 6, wherein the adjustable-length tube features a series of circumferential pleats adapted to be folded together when the adjustable-length tube is collapsed.

8. The retractable syringe needle of claim 1, wherein the adjustable-length tube comprises:

an outer tube having a first end which is adapted to be reversibly secured to the syringe barrel and a second end; and an inner tube having a fist end which is adapted to be secured to the hub and a second end;

wherein the second end of the inner tube is slidably disposed within the second end of said outer tube.

9. The retractable syringe needle of claim 8, wherein a leakproof seal is disposed between an outer surface of the inner tube and an inner surface of the outer tube.

10. The retractable syringe needle of claim 1, wherein the means to reversibly alter the length of the adjustable-length tube comprises:

a longitudinal slot running along the length of the tubular sheath;

a knob slidably engaging said longitudinal slot, said knob being rigidly connected with the second end of the adjustable-length tube;

a means for reversibly securing the knob at a first position along the length of the longitudinal slot, where the adjustable-length tube is contacted when the knob is in said first position;

a means for reversibly securing the knob at a second position along the length of the longitudinal slot, where the adjustable-length tube is extended when the knob is in said second position; and a means for reversibly sliding the knob from said first position to said second position.

11. The retractable syringe needle of claim 10, wherein the means for reversibly securing the knob at the first position comprises a second slot which intersects the longitudinal slot at said first position, said second slot being adapted to receive said knob; and wherein the means for reversibly securing the knob at the second position comprises a third slot which intersects the longitudinal slot at said second position, said third slot being adapted to receive said knob.

12. The retractable syringe needle of claim 1, additionally comprising a means to bias the hub away from the second end of the tubular sheath, causing the adjustable-length tube to be compressed.

13. The retractable syringe needle of claim 12, wherein the biasing means is a spring having a first end which contacts the hub, and a second end which contacts a circumferential ridge on the inner surface of the second end of the tubular sheath.

14. The retractable syringe needle of claim 1, wherein said tubular sheath comprises:

an anterior tubular sheath portion, said anterior portion having a first open end, and a second open end adapted to receive a hypodermic needle; and a posterior tubular sheath portion, said posterior portion having a first open end adapted to be rigidly connected with the first end of the adjustable-length tube, and a second open end;

wherein the first open end of the anterior portion is rigidly fastened to the second open end of the posterior portion.

15. The retractable syringe needle of claim 10, wherein said tubular sheath comprises:

an anterior tubular sheath portion, said anterior portion having a first open end, and a second open end adapted to receive a hypodermic needle; and a posterior tubular sheath portion, said posterior portion having a first open end adapted to be rigidly connected with the first end of the adjustable-length tube, and a second open end;

wherein the first open end of the anterior portion is rigidly fastened to the second open end of the posterior portion; and wherein the longitudinal slot runs continuously from a defined point on the anterior tubular sheath portion to a defined point on the posterior tubular sheath portion.

16. A retractable needle, comprising:

a) a hollow hypodermic needle;

b) a cylindrical hub having an axial passage therethrough, said hollow needle being rigidly connected with the hub so that the axial passage and the interior of the hollow needle form a continuous conduit;

c) a adjustable-length tube having a first end and a second end, said tube having a length which may be reversibly altered from a first contracted length to a second extended length;

d) a means for reversibly securing a tube adapted to carry intravenous fluids to the first end of the adjustable-length tube so that the interior of the syringe barrel is in fluid contact wit the interior of the adjustable-length tube;

e) a means for securing the cylindrical hub to the second end of the adjustable-length tube so that the interior of the hollow needle is in fluid contact with the interior of the adjustable-length tube;

f) a tubular sheath disposed around the adjustable-length tube; said tubular sheath having a first end which is rigidly connected with the first end of the adjustable-length tube and a second end having an opening which is sufficiently large to allow the end of the hypodermic needle to pass therethrough; and g) a means to reversibly alter the length of the adjustable-length tube from the contacted length to the extended length;

where the hypodermic needle is entirely disposed within the sheath when the adjustable-length tube is contracted, and where the end of the hypodermic needle is exposed through the opening in the second end of the sheath when the adjustable-length tube is extended.

17. The retractable needle of claim 16, wherein the means for securing the tube for carrying intravenous fluids to the first end of the adjustable-length tube is a hollow conical member having an inner surface and an outer surface, said inner surface defining a cavity adapted to frictionally engage a male joint on the tip of the tube for carrying intravenous fluid and said outer surface being rigidly secured to the first end of the tubular sheath;

said conical member having a narrow end with a passage therethrough, said narrow end being connected to the first end of the adjustable-length tube so that the frustoconical cavity makes fluid contact with the interior of the adjustable-length tube through the passage in the narrow end of the conical member.

18. A retractable syringe needle, comprising:

a) a hollow hypodermic needle;

b) a cylindrical hub having an axial passage therethrough, said hollow needle being connected with the hub so that the axial passage and the interior of the hollow needle form a continuous conduit;

c) an adjustable-length tube having a first end and a second end, said tube having a length which may be reversibly altered from a first contracted length to a second extended length;

d) a means for reversibly securing a syringe barrel to the first end of the adjustable-length tube so that the interior of the syringe barrel is in fluid contact with the interior of the adjustable-length tube;

e) a means for securing the cylindrical hub to the second end of the adjustable-length tube so that the interior of the hollow needle is in fluid contact with the interior of the adjustable-length tube;

f) a tubular sheath disposed around the adjustable-length tube; said tubular sheath having a first end which is rigidly connected with the first end of the adjustable-length tube and a second end having an opening which is sufficiently large to allow the end of the hypodermic needle to pass therethrough; and g) a means to reversibly alter the length of the adjustable-length tube from the contracted length to the extended length;

where the hypodermic needle is entirely disposed within the sheath when the adjustable-length tube is contracted, and where the end of the hypodermic needle is exposed through the opening in the second end of the when the adjustable-length tube is extended.

19. An assembly for administering hypodermic injections, comprising:

a) a syringe barrel;

b) a plunger slidably mounted within the syringe barrel;

c) a hollow hypodermic needle;

d) a cylindrical hub having an axial passage therethrough, said hollow needle being rigidly connected with the hub so that the axial passage and the interior of the hollow needle form a continuous conduit;

e) a adjustable-length tube having a first end and a second end, said tube having a length which may be reversibly altered from a first contracted length to a second extended length;

f) a means for reversibly securing the syringe barrel to the first end of the adjustable-length tube so that the interior of the syringe barrel is in fluid contact with the interior of the adjustable-length tube;

g) a means for securing the cylindrical hub to the second end of the adjustable-length tube so that the interior of the hollow needle is in fluid contact with the interior of the adjustable-length tube;

h) a tubular sheath disposed around the adjustable-length; and tubular sheath having a first end which is rigidly connected with the first end of the adjustable-length tube and a second end having an opening which is sufficiently large to allow the end of the hypodermic needle to pass therethrough; and i) a means to reversibly alter the length of the adjustable-length tube from the contracted length to the extended length;

where the hypodermic needle is entirely disposed within the sheath when the adjustable-length tube is contracted, and where the end of the hypodermic needle is exposed through the opening in the second end of the sheath when the adjustable-length tube is extended.

20. The retractable syringe needle of claim 19, wherein the means for securing the syringe barrel to the first end of the adjustable-length tube is a hollow member having an inner surface and an outer surface, said inner surface defining a frustoconical cavity adapted to frictionally engage a frustoconical tip on the syringe barrel and said outer surface being rigidly secured to the first end of the tubular sheath;

said member having a passage therethrough, said member being connected to the first end of the adjustable-length tube so that the frustoconical cavity makes fluid contact with the interior of the adjustable-length tube though the passage in the member.

21. An assembly for administering intravenous fluids, comprising:

a) a container adapted to hold fluids;

b) a conduit adapted to carry fluids from the container to a patient, said conduit having a first end connected to a container and a second end;

c) a hollow hypodermic needle;

d) a cylindrical hub having an axial passage therethrough, said hollow needle being rigidly connected with the hub so that the axial passage and the interior of the hollow needle form a continuous conduit;

e) a adjustable-length tube having a first end and a second end, said tube having a length which may be reversibly altered from a first contracted length to a second extended length;

f) a means for reversibly securing the second end of the conduit to the first end of the adjustable-length tube so that the interior of the conduit is in fluid contact with the interior of the adjustable-length tube;

g) a means for securing the cylindrical hub to the second end of the adjustable-length tube so that the interior of the hollow needle is in fluid contact with the interior of the adjustable-length tube;

h) a tubular sheath disposed around the adjustable-length tube; said tubular sheath having a first end which is rigidly connected with the first end of the adjustable-length tube and a second end having an opening which is sufficiently large to allow the end of the hypodermic needle to pass therethrough; and i) a means to reversibly alter the length of the adjustable-length tube from the contracted length to the extended length;

where the hypodermic needle is entirely disposed within the sheath when the adjustable-length tube is contracted, and where the end of the hypodermic needle is exposed through the opening in the second end of the sheath when the adjustable-length tube is extended.

22. A retractable syringe needle, comprising;

a) a needle assembly featuring a hypodermic needle; a hub being affixed to said needle; a means for securing a syringe barrel to said hub; and a pin connected with said hub;

b) a container having a tubular wall with a first open end adapted to receive a syringe barrel and a second open end adapted to receive a syringe needle, said container having the needle assembly slidably mounted therein so that the needle assembly may be moved from a first position where the needle is within the container to a second position where the needle is exposed by sliding the hub toward the second open end of the container and causing the needle to pass through the second open end;

said container being formed from:

i) an anterior container portion having a tubular wall, said anterior portion of said container having a first open end adapted to receive a syringe barrel; a second open end adapted to receive a hypodermic needle; and a first longitudinal slit running from the first end of the anterior portion of the container to a define point near the second end of the anterior portion of the container, and ii) a posterior container portion having a tubular wall, said posterior portion of said container having a first open end adapted to receive a syringe barrel and a second open end adapted to receive a syringe barrel, and a second longitudinal slit adapted to slidably engage said pin running from the first end of the posterior portion of the container to a defined point near the second end of the posterior portion of the container, where the anterior container portion ad the posterior container portion are joined together to form the container so that the needle assembly is inside the container and so that the first and second longitudinal slits cooperate to form a third slit which slidably engages said pin;

c) a means for biasing the needle assembly toward said first position;

d) a first means for releasably engaging the pin at a first defined location in said third slit so as to hold said needle assembly in said first position;

wherein said first means for releasably engaging the pin comprises a first notch which intersects said third slit at said first defined location, so that said needle assembly may be releasably held in said first position by sling said pin out of said longitudinal slit into said first notch; and e) a second means for releasably engaging the pin at a second defined location in said third slit so as to hold said needle assembly in said second position;

wherein said second means for releasably engaging the pin comprises a second notch which intersects said third slit at said second defined location, so that said needle assembly may be releasably held in said second position by sliding said pin out of said longitudinal slit into said second notch.

23. The retractable syringe needle of claim 22, wherein an entrance to each notch is narrower than the pin, yet broad enough that the pin can be pushed into the notch without undue effort.

24. The retractable syringe needle of claim 7, additionally comprising a means to bias the hub away from the second end of the tubular sheath, causing the adjustable-length tube to be comprised, wherein the biasing me is a spring having a first end which contacts the hub, and a second end which contacts a circumferential ridge on the inner surface of the second end of the tubular sheath.

25. The retractable syringe needle of claim 8, additionally comprising a means to bias the hub away from the second end of the tubular sheath, causing the adjustable-length tube to be compressed, wherein the biasing means is a spring having a first end which contacts the hub, and a second end which contacts a circumferential ridge on the inner surface of the second end of the tubular sheath.

26. A disposable hypodermic syringe needle, comprising:

a) a syringe needle assembly, containing a hypodermic needle, and a hub affixed to said needle;

b) an annular sleeve defining a frusto-conical cavity, said annular sleeve surrounding the periphery of the hub; wherein the cavity in the annular sleeve is adapted to frictionally engage a frusto-conical tip of a syringe barrel;

c) a container having a tubular wall containing said hypodermic needle, said container having:

a first end having an opening adapted to receive a syringe barrel;

a second end having an opening which is sufficiently large to receive the hypodermic needle, but too small to receive a syringe barrel; and a longitudinal slit through the wall of the container;

d) a spring which biases the annular sleeve away from the second end of the container so that the needle attached to the sleeve is container within the container while allowing the needle to pass through the opening of the second end of the container when the spring is compressed;

e) a knob connected with said annular sleeve, said knob being slidably engaged by the longitudinal slit through the wall of the container, and f) a means for reversibly engaging the knob when the spring is compressed;

wherein the knob is manufactured separately from the annular sleeve, and then is connected with the annular sleeve.

27. The disposable hypodermic syringe needle of claim 26, wherein said knob connected with said annular sleeve has a thumbrest attached thereto, said knob being slidably engaged by the longitudinal slit through the wall of the container, where said thumbrest is wider than said longitudinal slot and is positioned outside of said container; and wherein the knob having the thumbrest attached thereto is manufactured separately from said annular sleeve, and then is connected with said annular sleeve in such a way that the thumbrest is positioned outside of the container while said needle assembly is positioned inside of the container.

28. The disposable hypodermic syringe needle of claim 27, wherein the knob is connected with the annular sleeve by means of an adhesive.

29. The disposable hypodermic syringe needle of claim 27, wherein the knob is connected with the annular sleeve by:
  a) applying an adhesive to a threaded male joint on the knob, screwing the threaded male joint into a threaded female joint on the annular sleeve, and allowing the adhesive to bond the male joint to the female joint; or
  b) applying an adhesive to a threaded female joint on the annular sleeve, screwing a threaded male joint on the knob into the threaded female joint the sleeve, and allowing the adhesive to bond the male joint to the female joint; or
  c) applying an adhesive to a threaded male joint on the knob and to a threaded female joint on the annular sleeve, screwing threaded male joint into the threaded female joint, and allowing the adhesive to bond the male joint to the female joint.

30. The disposable hypodermic syringe needle of claim 27, wherein the knob is connected with the annular sleeve by screwing a threaded male joint on the knob into a threaded female joint on the annular sleeve.

31. The disposable hypodermic syringe needle of claim 26, wherein:
  the first end of the container has an opening adapted to receive a syringe barrel;
  the second end has an opening which is sufficiently large to receive the hypodermic needle, but too small to receive a syringe barrel; and
  the opening in the first end of the container and the opening in the second end of the container may each be covered by a cap.

32. A disposable hypodermic syringe needle, comprising:
  a) a syringe needle assembly, containing a hypodermic needle, and a hub affixed to said needle;
  b) an annular sleeve defining a cavity said annular sleeve surrounding the periphery of the hub; wherein the cavity in the annular sleeve is adapted to frictionally engage a fitting on a tip of a syringe barrel;
  c) a container having a tubular wall, where said syringe needle assembly is contained within the container, said container having:
    a first end of the container having an opening adapted to receive a syringe barrel;
    a second end of the container having an opening which is sufficiently large to allow the hypodermic needle to pass therethrough, but is too small to receive a syringe barrel; and
    a longitudinal slit through the wall of the container having an open first slit end extending to the first end of the container, and a second closed slit end near the second end of the container;
  d) a spring which biases the annular sleeve away from the second end of the container so that the needle connected with the sleeve is concealed within the container, while allowing the needle to pass through the opening in the second end of the container when the spring is compressed;
  e) a knob connected with said annular sleeve, said knob being slidably engaged boy the longitudinal slit through the wall of the container; and
  f) a means for reversibly engaging the knob when the spring is compressed; and
  g) a means for preventing the knob which slidably engages the slit from passing through the first open slit end.

33. The disposable hypodermic syringe needle of claim 32, wherein the means for preventing the knob from passing through the first open slit end comprises a non-elastic ring which is rigidly secured to the exterior surface of the first end of the container.

34. The disposable hypodermic syringe needle of claim 32, wherein the means for preventing the knob from passing through the first open slit end comprises a non-elastic ring which is adapted to slide over the exterior surface of the first end of the container, and then be rigidly secured to the exterior surface of the first end of the container.

35. The disposable hypodermic syringe needle of claim 32, wherein the means for preventing the knob from passing through the first open slit end comprises
  a) a non-elastic strap having a fist strap end and a second strap end, wherein the first strap end is connected to the exterior surface of the first end of the container on one side of the first open slit end, and wherein the strap is sufficiently long to allow the second strap end to reach the exterior surface of the fist end of the container on the other side of the first open slit end; and
  b) a means for securing the second strap end to the exterior surface of the first end of the container on the other side of the first open slit end.

36. The disposable hypodermic syringe needle of claim 32, wherein the knob is manufactured separately from the annular sleeve, and then is connected with said annular sleeve.

37. The disposable hypodermic syringe needle of claim 32, wherein the first open slit end of the longitudinal slit is large enough to admit the knob connected with said syringe needle assembly; and the means for preventing the knob which slidably engages the slit from passing through the first open slit end acts to prevent the knob from exiting the longitudinal slit through the first open slit end;
  wherein said knob may be used to move the hub from a first position remote from the second end of the container to a second position near the second end of the container; and
  wherein the hypodermic needle attached to the hub is contained within the container when the hub is in the first position, and where the hypodermic needle attached to the hub is exposed through the opening in the second end of the container when the hub is in the second position.

38. The disposable hypodermic syringe needle of claim 37, wherein the knob is manufactured separately from the annular sleeve, and then is connected with said annular sleeve.

39. A disposable hypodermic syringe needle, comprising:
  a) a syringe needle assembly, containing a hypodermic needle, a hub affixed to said needle, and an annular sleeve defining a cavity, said annular sleeve being connected to the periphery of the hub, wherein said annular sleeve is adapted to frictionally engage a fitting on the tip of a syringe barrel;
  b) a container having a tubular wall, said tubular wall having a diameter which is greater than the maximum diameter of the hub, where said syringe needle assembly is contained within the container, said container having:
    an inner diameter which is greater than a diameter of said hub;
    a first end having an opening adapted to receive a syringe barrel;
    a second end having an opening which is sufficiently large to allow the hypodermic needle to pass therethrough, but is too small to receive a syringe barrel; and a longitudinal slit through the wall of the container;

c) a knob having a thumbrest which is wider than said longitudinal slit connected thereto, said knob being connected with said annular sleeve and being slidably engaged by the longitudinal slit through the wall of the container so that said thumbrest is positioned on the exterior of said container, where said knob may be used to move the hub from a first position remote from the second end of the container to a second position near the second end of the container;

where the hypodermic needle attached to the hub is contained within the container when the hub is in the first position, and where the hypodermic needle attached to the hub is exposed through the opening in the second end of the container when the hub is in the second position;

d) a spring which biases the hub toward the first position, while allowing the hub to be moved into the second position when the spring is compressed;

e) a means for reversibly engaging the knob so as to hold the hub in the second position when the spring is compressed;

wherein said knob connected with said annular sleeve and said thumbrest cooperate to maintain said hub at a position along a longitudinal axis of the container.

40. The disposable hypodermic syringe needle of claim 39, wherein the knob is manufactured separately from the annular sleeve, and then is connected with the annular sleeve.

41. The disposable hypodermic syringe needle of claim 10, wherein the knob is connected with the second end of the adjustable-length tube by means of an adhesive.

42. The disposable hypodermic syringe needle of claim 41, wherein the knob is connected with the second end of the adjustable-length tube by screwing a threaded male joint on the knob into a threaded female joint on the hub, said hub being connected to the second end of the adjustable-length tube.

43. The disposable hypodermic syringe needle of claim 42, wherein the knob is connected with the second end of the adjustable-length tube by:

a) applying an adhesive to a threaded male joint on the knob, screwing the threaded male joint into a threaded female joint on the hub, and allowing the adhesive to bond the male joint to the female joint; or b) applying an adhesive to a threaded female joint on the hub, screwing a threaded male joint on the knob into the threaded female joint on the hub, and allowing the adhesive to bond the male joint to the female joint; or c) applying an adhesive to a threaded male joint on the knob and to a threaded female joint on the hub, screwing the threaded male joint into the threaded female joint, and allowing the adhesive to bond the male joint to the female joint.

44. The disposable hypodermic syringe needle of claim 10, wherein the tubular sheath has:

a first end which is rigidly connected with the first end of the adjustable-length tube;

a second end having an opening which is sufficiently large to allow the end of the hypodermic needle to pass therethrough; and a longitudinal slot running along the length of the tubular sheath, said slot being closed at both ends.

45. The disposable hypodermic syringe needle of claim 10, wherein the tubular sheath has:

a first end which is rigidly connected with the first end of the adjustable-length tube;

a second end having an opening which is sufficiently large to allow the end of the hypodermic needle to pass therethrough; and a longitudinal slot running along the length of the tubular sheath, said slot having a first open end extending to the first end of the tubular sheath, and a second closed end near the second end of the tubular sheath; and a means for preventing the knob engaging the slot from passing through the first open end of the slot.

46. The disposable hypodermic syringe needle of claim 45, wherein the means for preventing the knob engaging the slot from passing through the first open end of the slot comprises a hollow conical member having an inner surface and an outer surface, said inner surface defining a frustoconical cavity adapted to frictionally engage the frustoconical tip of the syringe barrel and said outer surface being rigidly secured to the interior surface of the first end of the tubular sheath.

47. The disposable hypodermic syringe needle of claim 1, wherein:

each end of the tubular sheath may be covered by a cap.

* * * * *